United States Patent [19]
Kimura et al.

[11] Patent Number: 4,816,909
[45] Date of Patent: Mar. 28, 1989

[54] VIDEO ENDOSCOPE SYSTEM FOR USE WITH DIFFERENT SIZES OF SOLID STATE DEVICES

[75] Inventors: Kenji Kimura, Tachikawa; Masao Uehara, Hachioji; Hiroki Hibino, Hachioji; Akinobu Uchikubo, Hachioji; Jun Hasegawa, Hino; Masahide Kanno, Hachioji; Shinji Yamashita, Hachioji; Masahiko Sasaki, Hachioji; Katuyoshi Sasagawa, Hachioji, all of Japan

[73] Assignee: Olympus Optical Co., Ltd., Tokyo, Japan

[21] Appl. No.: 134,627

[22] Filed: Dec. 16, 1987

[30] Foreign Application Priority Data

| Jan. 28, 1987 | [JP] | Japan | 62-17982 |
| Aug. 10, 1987 | [JP] | Japan | 62-199399 |
| Oct. 20, 1987 | [JP] | Japan | 62-266061 |
| Oct. 20, 1987 | [JP] | Japan | 62-266059 |
| Dec. 17, 1987 | [JP] | Japan | 61-300755 |

[51] Int. Cl.[4] .......... A61B 1/04; A04N 7/18
[52] U.S. Cl. .......... 358/98; 358/42; 128/6
[58] Field of Search .......... 358/98, 166, 37, 29; 128/4, 6

[56] References Cited

U.S. PATENT DOCUMENTS

| 4,593,313 | 6/1986 | Nagasaki et al. | 358/98 |
| 4,656,508 | 4/1987 | Yokota | 358/98 |
| 4,667,229 | 5/1987 | Cooper et al. | 358/98 |
| 4,737,842 | 4/1988 | Nagasaki et al. | 358/98 X |

FOREIGN PATENT DOCUMENTS

| 2515148 | 10/1976 | Fed. Rep. of Germany . |
| 3109258 | 3/1982 | Fed. Rep. of Germany . |
| 3429811 | 4/1985 | Fed. Rep. of Germany . |
| 61-48333 | 3/1986 | Japan . |
| 61-163316 | 7/1986 | Japan . |

Primary Examiner—James J. Groody
Assistant Examiner—Victor R. Kostak
Attorney, Agent, or Firm—Armstrong, Nikaido Marmelstein & Kubovcik

[57] ABSTRACT

An endoscope contains or is externally fitted with a color imaging device using a solid state imaging device and a signal processing device processing a signal for the endoscope. The color imaging device and solid state imaging device are provided so that the number of pixels and the kind of spectral characteristic of the color imaging device of the endoscope to be connected may be discriminated to process the signal even for the endoscopes having number of pixels and the spectral characteristic.

40 Claims, 33 Drawing Sheets

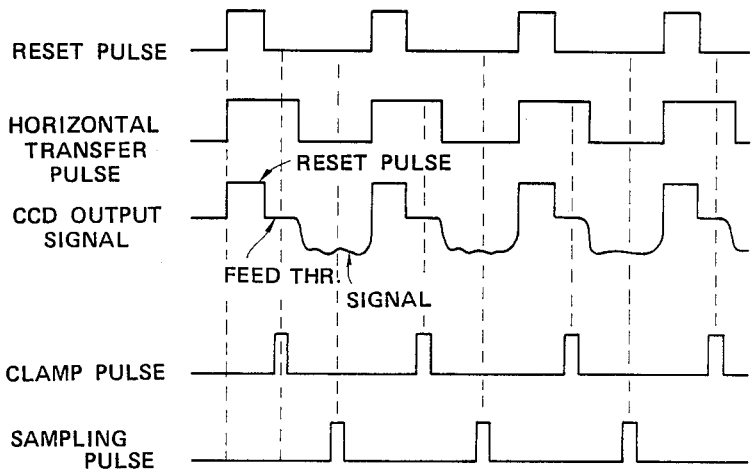
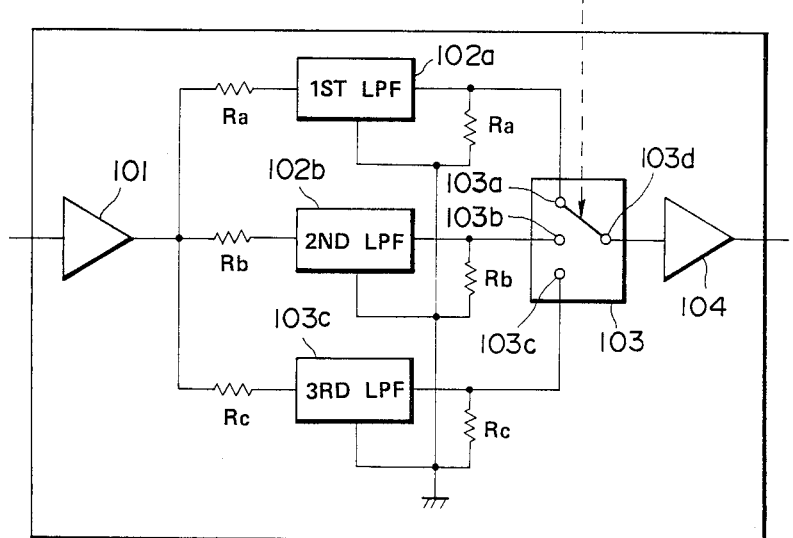

FIG.17
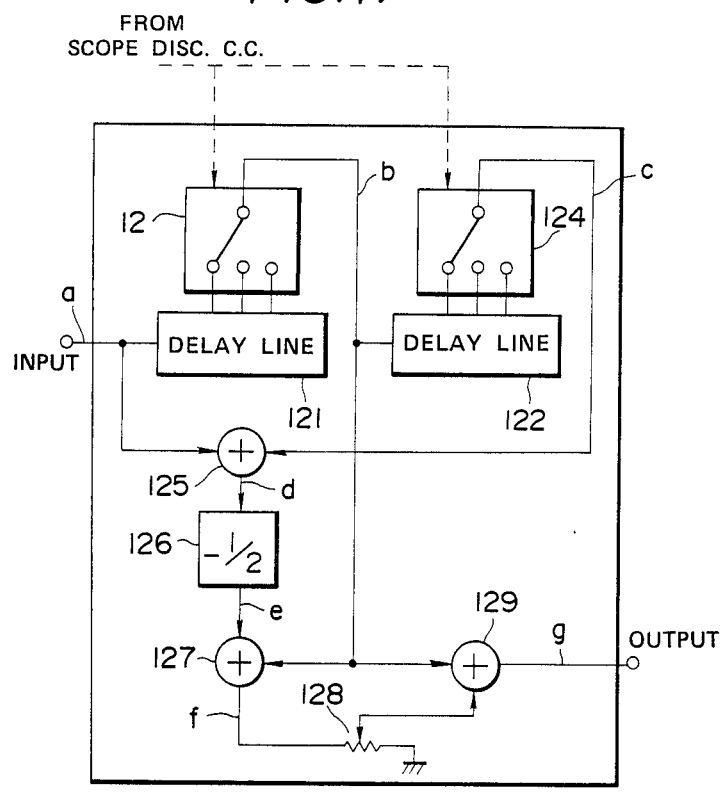
FIG.18a
FIG.18b
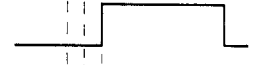
FIG.18c
FIG.18d
FIG.18e
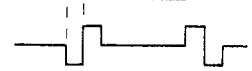
FIG.18f
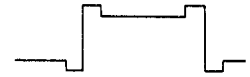
FIG.18g

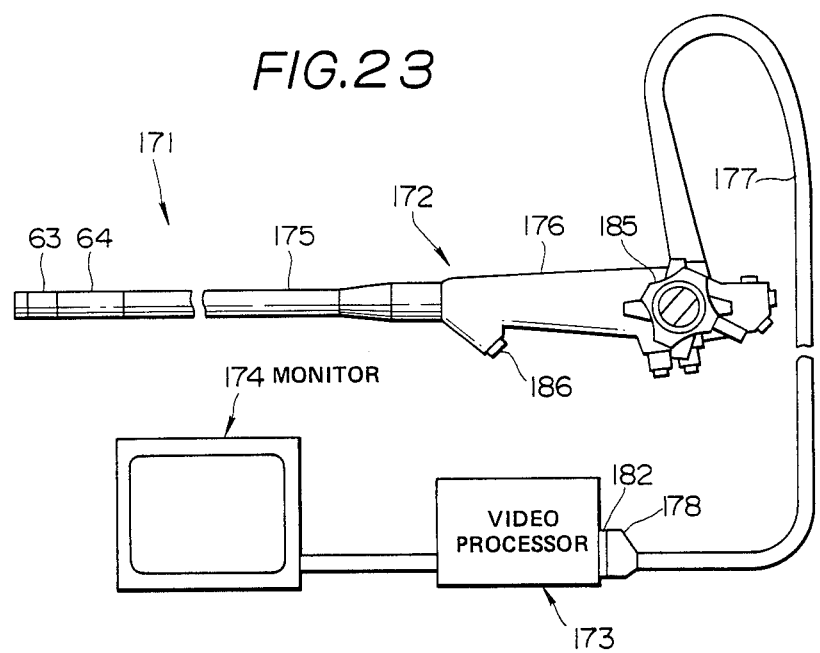
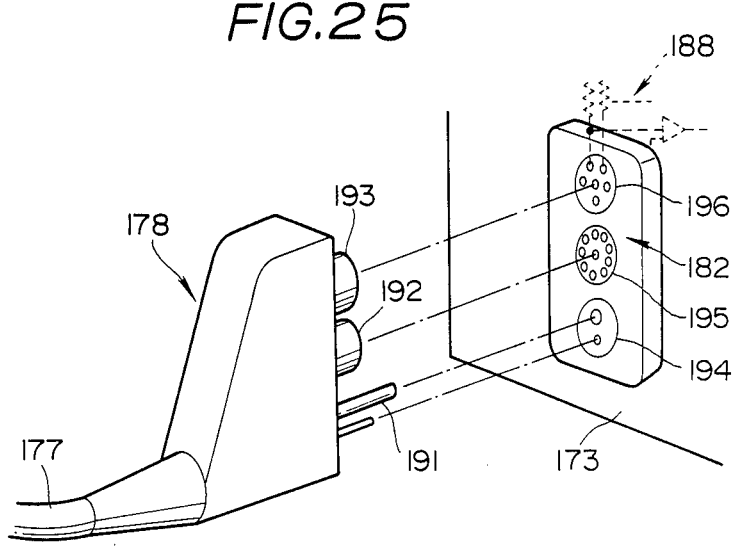

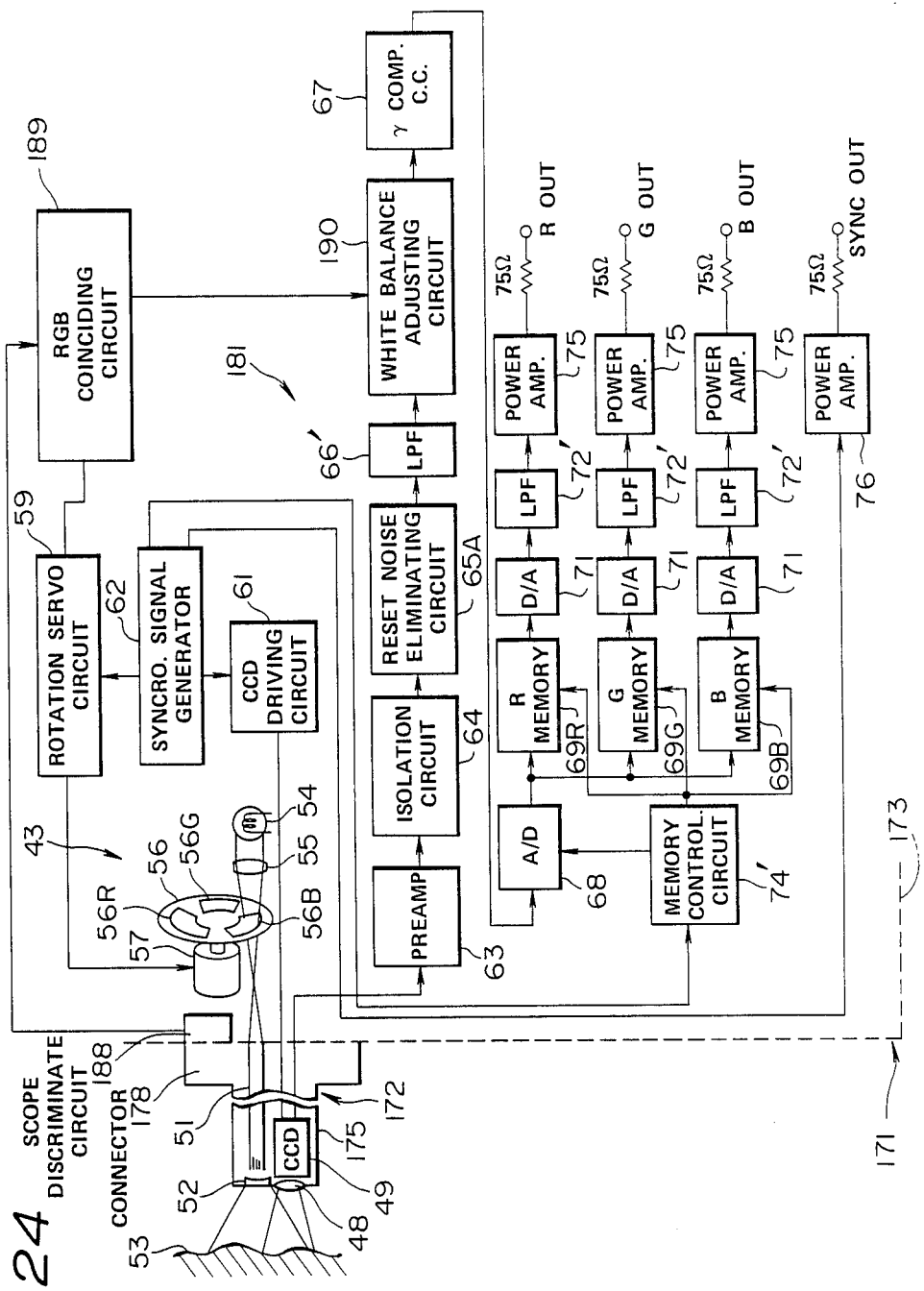

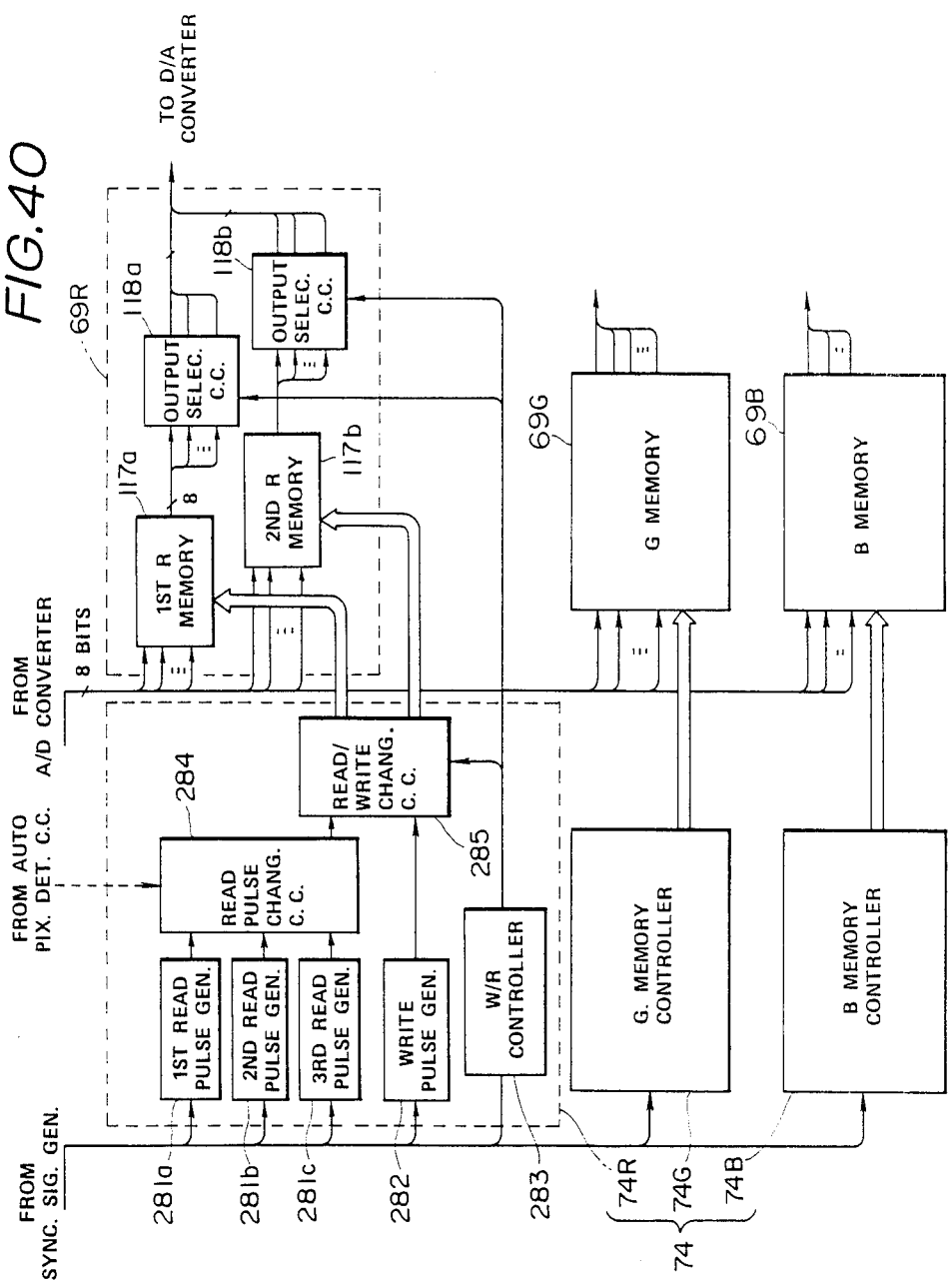

FIG.50
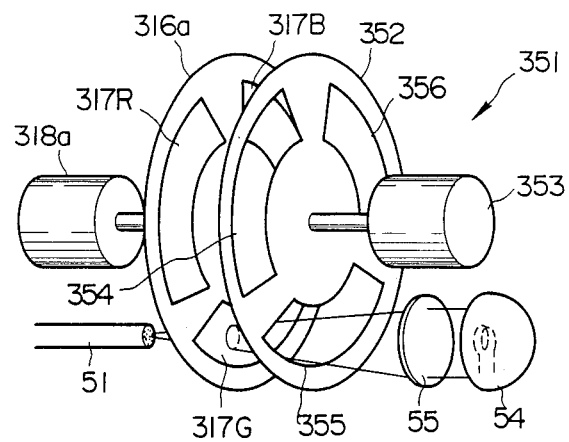
FIG.51a  FIG.51b  FIG.51c
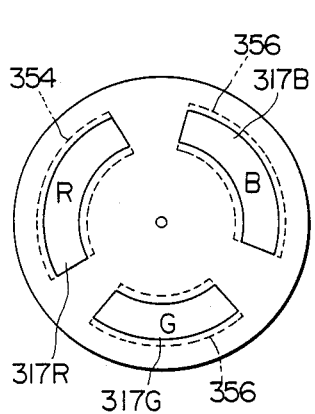 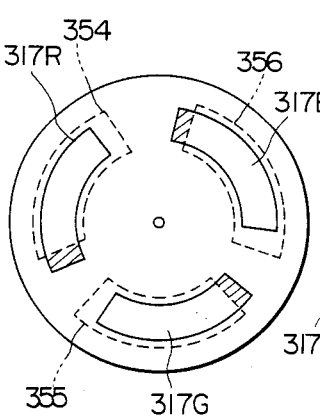 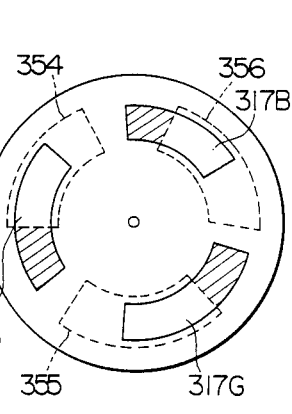

FIG.53a INPUT V. SYN. SIG VD TO PHASE DET. 369

FIG.53b INPUT P.G. PULSE TO PHASE DET. 369

FIG.53c INPUT V. SYN. SIG VD TO PHASE DET. 369'

FIG.53d INPUT P.G. PULSE TO PHASE DET. 369'

VIDEO ENDOSCOPE SYSTEM FOR USE WITH DIFFERENT SIZES OF SOLID STATE DEVICES

BACKGROUND OF THE INVENTION

Field of the Invention and Related Arm Statement

This invention relates to a video endoscope system having a signal processing means which can respond to different types of imaging means.

Recently, there has come to be extensively used an optical type endoscope provided with an observing optical system wherein an optical image is formed on the entrance end surface of an image guide by an objective arranged on the tip side of an elongated insertable part and is transmitted to the exit end surface arranged on the eyepiece side through this image guide.

Also, recently, there has been practiced an electronic type endoscope provided with an imaging means whereby an optical image is formed on the imaging surface of a solid state imaging device by an objective without using an image guide and is photoelectrically converted by this solid state imaging device.

Also, a television camera having a built-in imaging means is fitted to the eyepiece part of the above mentioned optical type endoscope so as to color-display the image.

The solid state imaging device forming the above mentioned imaging means has preferably many picture elements from the viewpoint of the resolution. However, in case the solid state imaging device is contained in the tip part of the insertable part inserted into a body cavity, the imaging device must be small.

As the outside diameter of the insertable part is different depending on the uses, the number of picture elements (or pixels) of the solid state imaging device to be fitted may be different.

Further, even if the number of picture elements is the same, due to the dispersion or improvement of the solid state imaging device, such spectral characteristic as the sensitivity may be different.

Therefore, in U.S. Pat. No. 4,667,229, an output signal level adjusting means or displaying position dispersion adjusting means is provided so that the output signal level may be identical even for a different type solid state imaging device.

However, the above mentioned U.S. patent can not respond to the case of a different number of picture elements.

OBJECTS AND SUMMARY OF THE INVENTION

An object of the present invention is to provide a video endoscope system whereby, even in case the number of picture elements or pixels is different, a video signal imaged by an imaging device can be color-displayed in a display.

Another object of the present invention is to provide a video endoscope system whereby, even in case the imaging device is different, the color tone of an imaged object can be faithfully color-reproduced.

In the present invention, on the endoscope side containing or externally fitted with a color imaging device using a solid stage imaging device, an information signal device relating to its spectral characteristic is provided and, on the signal processing apparatus side to which this endoscope is connected, an information signal decoding device is provided to variably control a gain for a plurality of color signals to produce a white-balanced color video signal. In the signal processing apparatus, the number of picture elements of the solid state imaging device in the connected endoscope is detected by the information signal of the information signal device relating to the number of picture elements or automatically so that the signal may be processed in response to the connected number of picture elements.

BRIEF DESCRIPTION OF THE DRAWINGS

FIG. 1 is a schematic formation view of a video endoscope system of the first embodiment.

FIG. 2 is a block diagram showing the formation of a driving circuit.

FIG. 3 is a switching circuit diagram.

FIG. 4 is a block diagram showing a modification of an electronic type endoscope controlling unit.

FIG. 5 is a formation diagram showing a discriminating means of a connected electronic scope.

FIGS. 10 to 18 relate to the fourth embodiment of the present invention.

FIG. 10 is a formation diagram of a video endoscope system of the fourth embodiment of the present invention.

FIGS. 11a–11c are circuit diagrams showing a video endoscope picture element number type discriminating means.

FIG. 12 is a circuit diagram of a scope discriminating circuit discriminating a video endoscope connected by the discriminating means in FIG. 11.

FIG. 13 is a block diagram showing the formations of a CCD driving circuit and a clamping pulse and sampling pulse generating circuit.

FIGS. 14a–14e are timing charts showing how a CCD output signal is read out by a double sampling process.

FIG. 15 is a block diagram showing the formation of a low-pass filter.

FIG. 16 is a block diagram showing the formation of a memory controlling circuit.

FIG. 17 is a formation diagram of a horizontal outline enhancing circuit.

FIG. 18 is an explanatory diagram of the operation in FIG. 17.

FIG. 23 is a side view showing the formation of the sixth embodiment of the present invention.

FIG. 24 is a block diagram showing the concrete formation of the sixth embodiment.

FIG. 25 is a perspective view showing a connector.

FIG. 40 is a formation diagram of a memory controlling circuit.

FIG. 50 is a perspective view showing a light source means in the fourteenth embodiment of the present invention.

FIGS. 51a–51c are explanatory views showing how a color filter is intercepted by a light intercepting part in response to a different number of picture elements.

FIGS. 53a and 53b are explanatory diagrams of the operation of the exposure time controlling means.

DETAILED DESCRIPTION OF PREFERRED EMBODIMENTS

Figure 1:
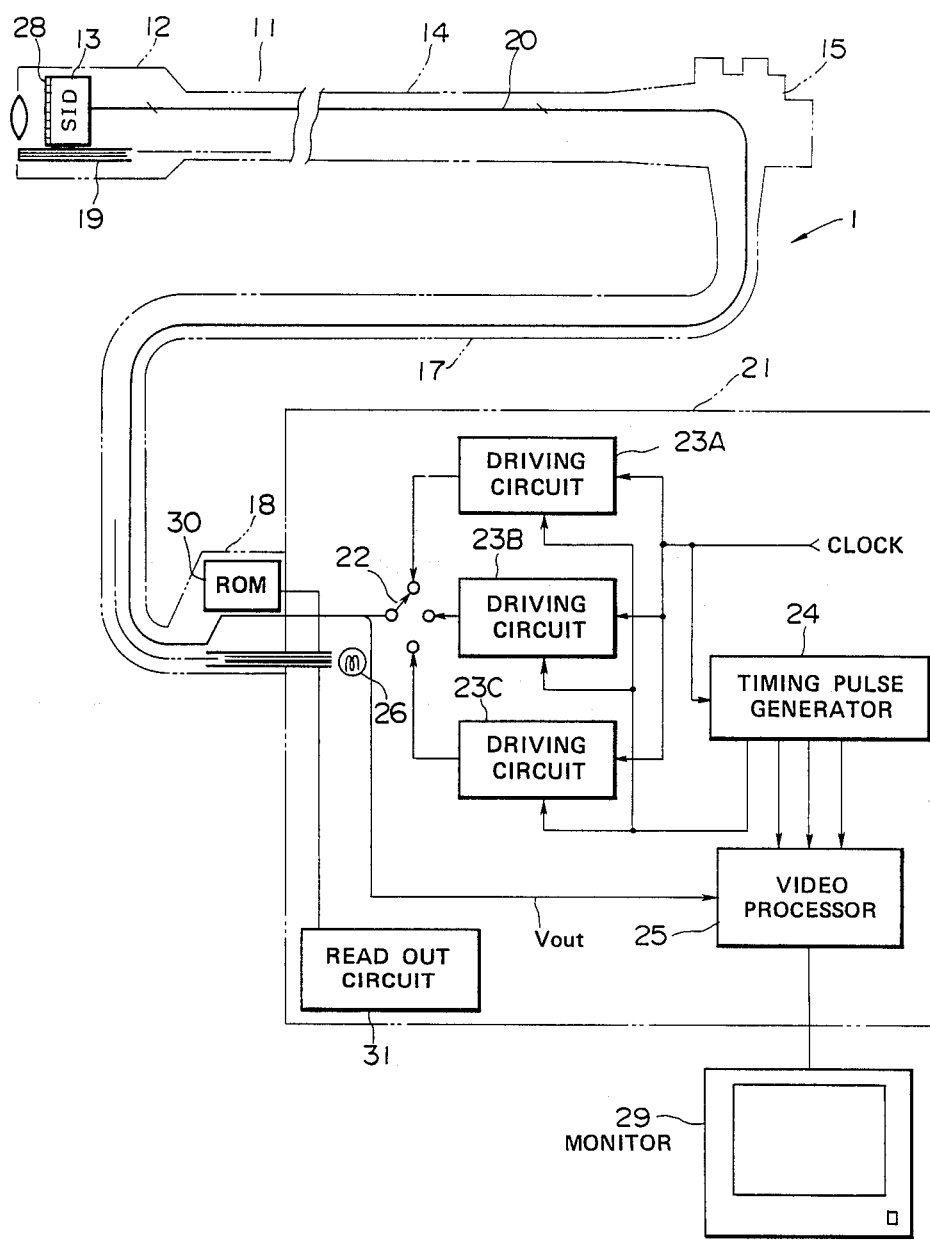
FIGS. 1 to 5 relate to the first embodiment of the present invention.

In a video endoscope system 1 of the first embodiment, a solid state imaging device 13 is built into a tip part 12 of an electronic endoscope 11. A plurality of signal lines 20 are led from the solid state imaging device 13 to an endoscope connection 18 together with an illuminating light leading light guide fiber bundle 19 through an endoscope insertable part 14, operating part 15 and universal cord 17. A white light is fed by a lamp 26 to the entrance end of the light guide fiber bundle 19. A mosaic-like color filter 28 is arranged on the imaging surface of the solid state imaging device 13. That is to say, the electronic endoscope 11 has a built-in type color imaging color filter with a white color illumination.

Figure 2:
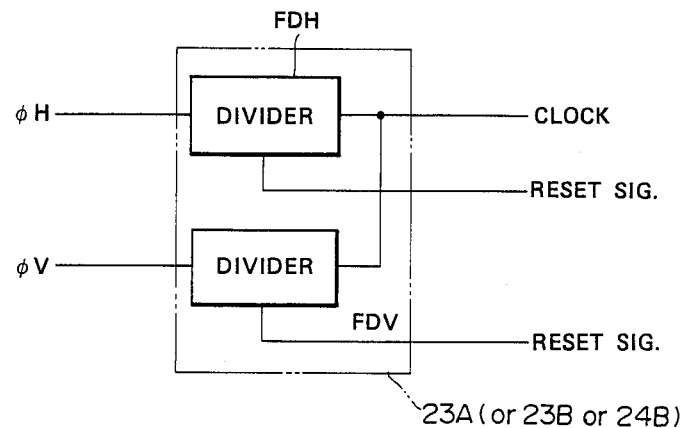
Figure 3:
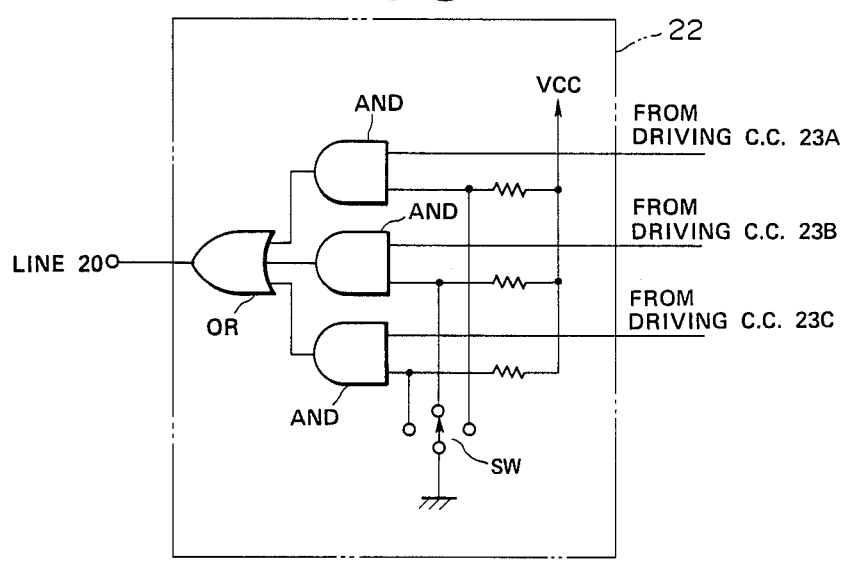

The endoscope connector 18 is fitted to an electronic type endoscope controlling unit 21. The signal lines 20 are connected to a three-step switching switch 22. The three contacts of the switch 22 are connected respectively to driving circuits 23A, 23B and 23C. Each of these driving circuits 23A, 23B and 23C is formed of frequency dividers $FD_H$ and $FD_V$ as shown in FIG. 2, is reset by a timing pulse from a timing pulse generator 24, divides a clock signal and outputs a driving signal of horizontal and vertical transfer pulses $\Phi_H$ and $\Phi_V$. The driving circuits 23A, 23B and 23C output respectively driving signals adapted to drive respectively solid state imaging devices having respectively, for example, 100,000, 50,000 and 20,000 picture elements or pixels, that is, driving signals of frequencies of 10 MHz, 5 MHz and 2 MHz. These driving signals are selectively led to the solid state imaging device 13 of the electronic type endoscope 11 through the switch 22. As shown in FIG. 3, the switch 22 is formed of an OR gate to which the line 20 is connected at the output end and three AND gates connected respectively to the input end of the OR gate. Input terminals on one side of the AND gates are connected respectively to the driving circuits 23A, 23B and 23C and input terminals on the other side are connected respectively to the contacts of a switching switch SW. The switching switch SW is switched in response to the type of the electronic type endoscope.

A video signal output line V out of the solid state imaging device 13 is connected to a video processor 25 which receives a timing signal of the timing pulse generator 24 and processes a video signal in response to the number of picture elements of the solid state imaging device. The output of the video processor 25 is connected to a monitor 29.

In the embodiment in FIG. 1, in case a large diameter electronic type endoscope, for example, an electronic type endoscope 11 having a built-in solid state imaging device 13 of 100,000 picture elements or pixels, is connected to the electronic type endoscope controlling unit 21, the switching switch 22 will be switched to select the driving circuit 23A. The driving circuit 23A outputs a driving signal of 10 MHz which is input into the solid state imaging device 13 of 100,000 picture elements through the signal line 20. The solid state imaging device 13 is driven by the driving signal of 10 MHz and outputs a video signal corresponding to 100,000 picture elements. The video signal is input into the video processor 25 through the video signal line V out. In the video processor 25, the video signal is controlled by the timing signal of the timing pulse generator and is processed to output a television signal.

Next, when a medium diameter electronic type endoscope, that is, an electronic type endoscope having a built-in solid imaging device having 50,000 picture elements is connected to the electronic type endoscope controlling unit 21, the switching switch 22 will be switched to select the driving circuit 23B. Therefore, the solid state imaging device 13 of 50,000 picture elements is driven by a driving pulse of 5 MHz to output a video signal corresponding to 50,000 picture elements.

In the same manner, in case a fine diameter electronic type endoscope, that is, an electronic type endoscope of 20,000 picture elements is connected to the electronic type endoscope controlling unit 21, a video signal corresponding to 20,000 picture elements will be output from the solid state imaging device 13.

As explained above, as the driving condition of the solid state imaging device can be selected in response to the type of the electronic type endoscope, that is, the number of picture elements of the solid state imaging device, various kinds of electronic type endoscopes can be controlled under the optimum conditions.

Figure 4:
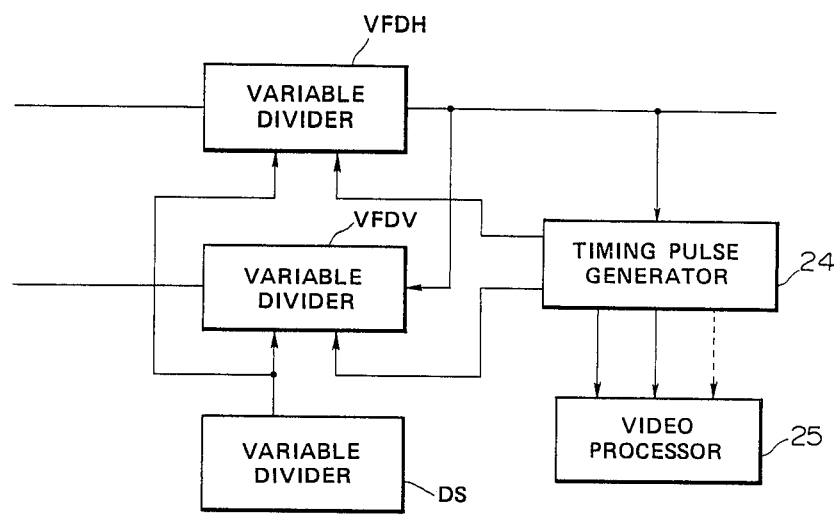

FIG. 4 shows an electronic type endoscope controlling unit in which each of the driving circuits 23A, 23B and 23C is formed of variable frequency dividers VFDH and VFDV. The variable frequency dividers VFDH and VFDV are formed, for example, of programmable counters and have the frequency dividing ratio varied by an N bit digital switch DS forming a frequency dividing ratio setting circuit. The frequency dividing ratio is determined by the type of the electronic type endoscope 11 and the digital switch DS is switched in response to the discrimination of the type of the electronic type endoscope. The digital switch DS inputs the output of N bits representing the type of the electronic type endoscope, that is, the number of picture elements of the solid state imaging device into the variable frequency dividers (programmable counters) VFDH and VFDV. Thereby, the variable frequency dividers VFDH and VFDV output horizontal and vertical transfer pulses of the frequency corresponding to the number of picture elements.

Figure 5:
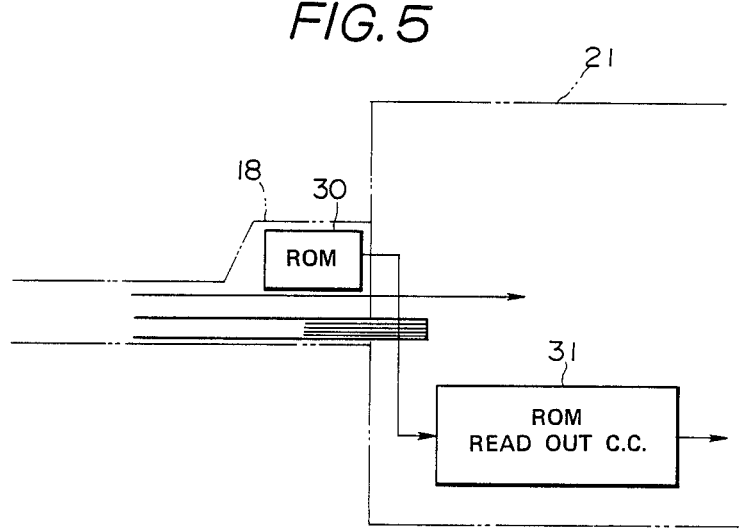

In order to discriminate the type of the electronic type endoscope 11, as shown in FIG. 5, a ROM 30, storing the information showing the type of the electronic type endoscope 11, is provided in the endoscope connector 18. The ROM 30 is connected to a ROM read-out circuit 31 provided in the electronic type endoscope unit 21, to read out the electronic type endoscope type information. By the electronic type endoscope type information read out by the ROM read-out circuit 31, the switching switch 22 shown in FIG. 1 and the switch SW shown in FIG. 3 are switched.

According to the thus formed video endoscope system of the first embodiment, even in case a video endoscope of a different number of picture elements is connected, the connected video endoscope will be discriminated. By this discrimination, the signal imaged by the solid state imaging device 13 is read out under the driving conditions adapted to the number of picture elements of the solid state imaging device 13 built in the connected video endoscope.

Figure 6:
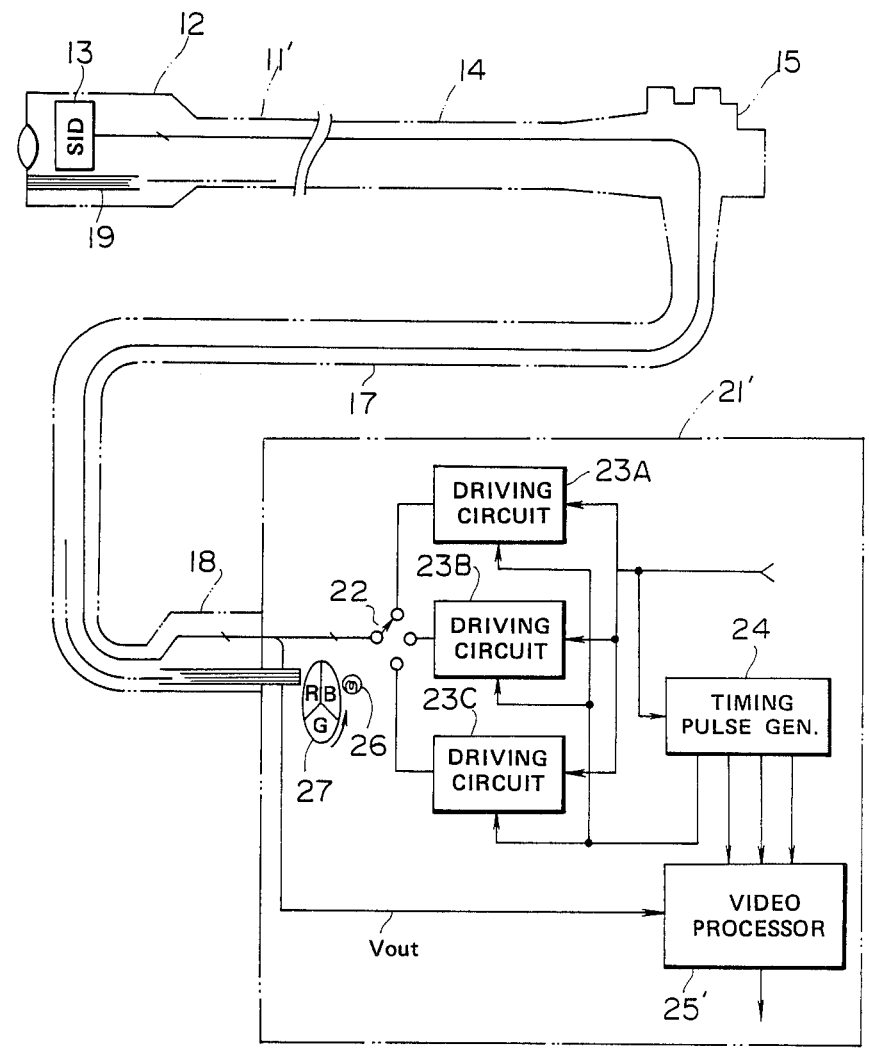
FIG. 6 is a schematic formation diagram of a frame sequential type video endoscope system.

FIG. 6 shows the second embodiment color-imaging under a frame sequential illumination.

In the frame sequential system, a three-color (R, G and B) divided filter 27 is arranged between a light source lamp 26 and a light guide fiber bundle 19 of an electronic type endoscope 11' so that, when the filter 27 is rotated, red, blue and green lights will be sequentially led, for example, at intervals of 1/90 second into a body cavity through the light guide fiber bundle 19. Therefore, the solid state imaging device 13 outputs sequentially, for example, at intervals of 1/90 second R, G and B video signals to one picture surface. The R, G and B video signals are input into a frame sequentially processing video processor 25'.

Figure 7:
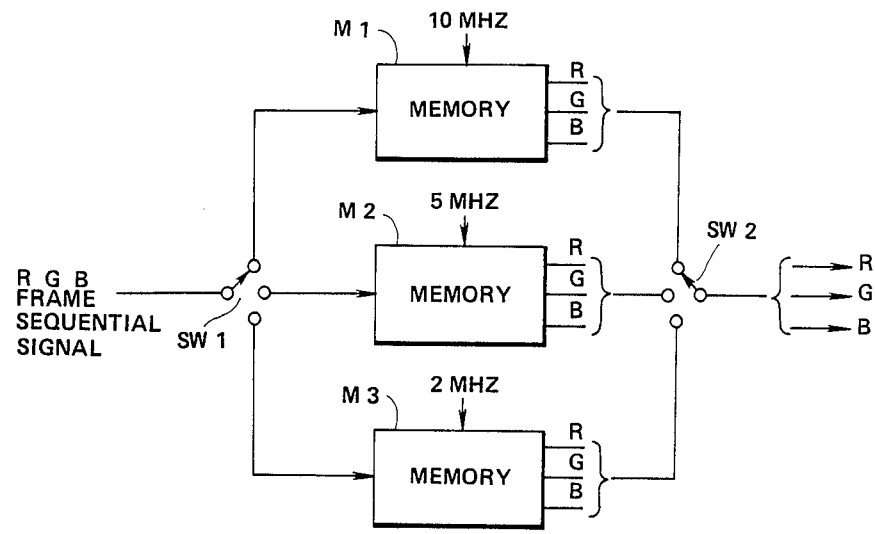
FIG. 7 is a block diagram showing memories switchable in response to the number of picture elements or pixels.

As shown in FIG. 7, the video processor 25' has an input switching switch SW1, frame memories M1, M2 and M connected respectively to the contact of the switch W1 and an output switching switch SW2. The input switching switch SW1 and output switching switch SW2 are switched in response to the type of the electronic type endoscope and the R, G and B video signals input into the video processor 25 are selectively input into the memories M1 to M3. For example, in case an electronic type endoscope of type A is connected to an electronic type endoscope controlling unit 21, the reading and writing will be controlled by a clock of 10 MHz and the R, G and B video signals will be sequentially stored in the memory M1 having a memory capacity of 100,000 picture images. The R, G and B video signals stored in the memory M1 are simultaneously read out and are output as color video signals through the output switching switch SW2.

Figure 8:
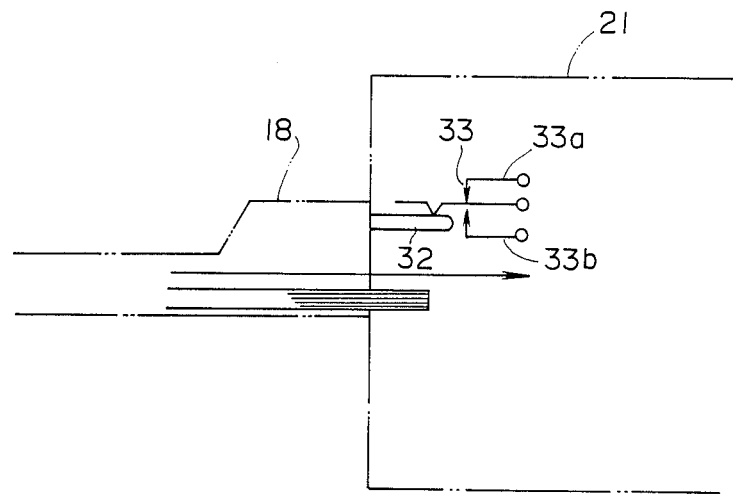
FIG. 8 is a formation diagram showing a discriminating means of a connected electronic scope.

In the video endoscope 11', as shown in FIG. 8, the scope connector 18' is provided with a means of mechanically discriminating the type of the video endoscope 11'. In FIG. 8, two kinds of types are discriminated depending on whether the connector 18' is provided with a pin 32 or not. For example, the electronic type endoscope of type A is provided with the pin 32 but the electronic type endoscope of type B is provided with no pin. Whether there is a pin 32 or not is detected by a switch mechanism 33. That is to say, in the case of the type A, the contact 33a will be closed. In the case of the type B, the contact 33b will be closed. The type of the electronic type endoscope can be recognized by the closure of either of the contacts 33a and 33b. A discriminating signal which can discriminate three or more types of video endoscopes can be produced by increasing the number of the above mentioned pins 32 and switch mechanisms 33. The switch 22 in FIG. 6 and the switches SW1 and SW2 in FIG. 7 are switched by the discriminating signal. Thus, the driving conditions and signal process adapted to the number of picture elements of the solid state imaging device of the connected video endoscope can be selectively set.

Figure 9:
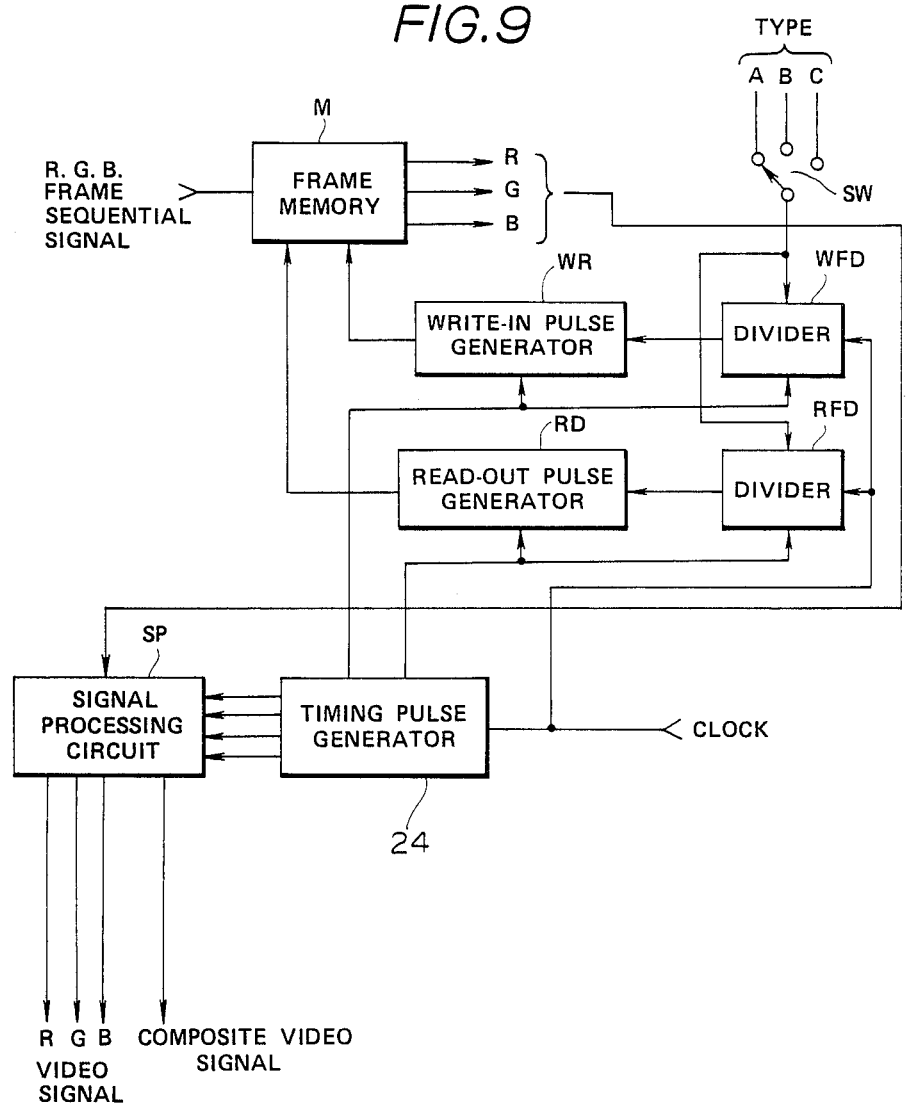
FIG. 9 is a block diagram showing an essential part of the third embodiment of the present invention.

FIG. 9 shows an essential part of the third embodiment of the present invention. In this embodiment, in a frame sequential system, one frame memory M is used in common for storing video signals from a plurality of types of electronic endoscopes. That is to say, a video signal line V out is connected directly to the memory M. A write-in pulse generator WR and read-out pulse generator RD are connected to the write-in and read-out terminals of the memory M. The write-in and read-out pulse generators WR and RD are connected to the output ends of frequency dividers WFD and RED. The frequency dividing ratio of the frequency dividers WFD and RFD is varied by a selecting signal obtained through an electronic type endoscope type switching switch SW and a clock signal is divided in the frequency in response to the frequency dividing ratio.

In the embodiment in FIG. 9, in case the electronic type endoscope, for example, of the type A is used, the frequency dividers WFD and RFD will have the frequency ratio set by a signal through the switch SW so as to output a signal of a frequency required to read and write a video signal corresponding to 100,000 picture elements. When the output signals of the frequency dividers WFD and RFD are input into the write-in and read-out pulse generators WR and RD, the write-in and read-out pulse generator WR and RD will input a write-in pulse or read-out pulse into the memory M and will control the memory M in writing-in or reading-out. That is to say, in writing-in R, G and B frame sequential video signals corresponding to 100,000 picture elements are written into the memory M as synchronized with the write-in pulse of the frequency determined by the frequency dividing ratio of the frequency divider WFD. In reading out, R, G and B video signals corresponding to 100,000 picture elements are simultaneously read out of the memory M as synchronized with the read-out pulse of the frequency determined by the frequency dividing ratio of the frequency divider RFD.

The video signal read out of the memory M is input into a signal processing circuit SP and is processed. The signal processing circuit SP outputs R, G and B video signals to a monitor so as to be displayed as a color picture image. The signal processing circuit SP outputs a composite video signal which is fed to a picture image recording apparatus (not illustrated). The write-in and read-out pulse generators WR and RD and the frequency dividers WFD and RFD are reset at intervals of 1 frame by the timing pulse from the timing pulse generator 24.

The timing of the write-in and read-out of the memory M is varied in response to the type set by the type switching switch SW as mentioned above so that the video signals obtained from a plurality of types of electronic endoscopes may be processed with only one memory. The type switching switch SW can be automatically switched in response to the type detection by such electronic type endoscope type detecting means as is shown in FIGS. 7 and 8.

In the case of the frame sequential system, as R, G and B are sequentially switched, the number of picture elements of the solid state imaging device may be $\frac{1}{3}$ as compared with the ordinary system requiring picture elements on all of R, G and B for one solid state imaging device.

According to the above mentioned first to third embodiments, as the solid state imaging device built in the tip part of an electronic type endoscope and having the number of picture elements determined in response to the diameter of the electronic type endoscope is driven and controlled by a driving signal corresponding to the number of picture elements, various electronic type endoscopes can be operated always under the optimum conditions.

Figure 10:
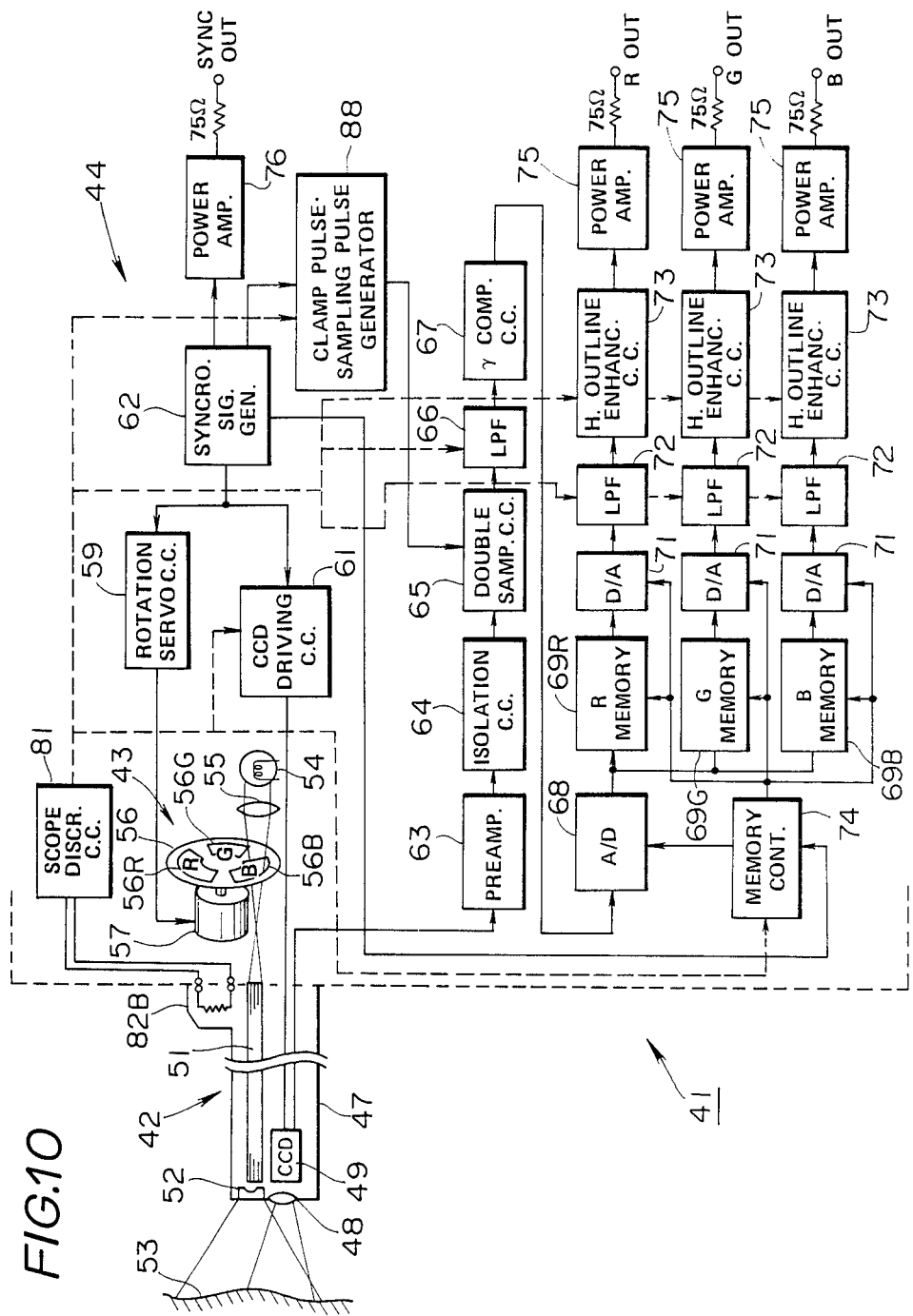

FIG. 10 shows a video endoscope system of the fourth embodiment of the present invention.

As shown in FIG. 10, a video endoscope system 41 of the fourth embodiment comprises an electronic endoscope (abbreviated as electronic scope) 42 having a built-in imaging means, a light source part 43 feeding an illuminating light to the electronic scope 42, a signal processing part 44 converting a signal imaged in the electronic scope 42 to a video signal which can be displayed in a displaying apparatus, a video processor 46 containing a controlling means processing the signal in response to the fitted electronic scope 42 and a monitor (not illustrated).

In the above mentioned electronic scope 42, an elongated insertable part 47 is formed so as to be easy to insert into a body cavity and an imaging means having an objective 48 and a CCD 49 as a solid state imaging device arranged on the tip side of the insertable part 47 is incorporated.

A light guide 51 transmitting an illuminating light is inserted through the above mentioned insertable part 47 so that the illuminating light fed from the light source part 43 may be transmitted through the light guide 51, emitted from the tip surface and expanded by a light distributing lens to illuminate the imaged object 53 side.

The light source part 43 feeding an illuminating light to the base side end surface of the above mentioned light guide 51 comprises a light source lamp 54, a lens 55 condensing and radiating the illuminating light from the light source lamp 54 onto the end surface of the light guide 51, a rotary filter 56 interposed in the light path between the lens 55 and the end surface of the light guide 51 and a motor 57 rotating and driving the rotary filter 56.

The above mentioned light source lamp 54 is such white light light source such as a xenone lamp. On the other hand, in the above mentioned rotary filter 56, red, green and blue respectively transmitting filters 56R, 56G and 56B respectively transmitting the lights of respective wavelength ranges of red, green and blue, that is, R, G and B are formed to be fan-like so that, when the rotary filter is rotated, the object may be illuminated frame sequentially with the respective lights of R, G and B primary colors. A motor 57 rotating the rotary filter 56 is controlled in the rotation by a rotation servo circuit 59. The motor 57 includes a rotation number detecting pulse generator and a rotation phase detecting pulse generator. By the rotation servo circuit 59, the rotation of the motor 57 is synchronized in the phase with the frame frequency (29.97 Hz in the case of the NTSC system) of the video signal.

The object 53, illuminated frame-sequentially by the respective lights of the above mentioned R, G and B, is made to form an image on the imaging surface of the CCD 49 by the objective 48. A signal photoelectrically converted by the application of a driving pulse transferred by a CCD driving circuit 61 to read out the signal, is read out. The driving pulse and the rotation servo circuit 59 operate as synchronized with a reference signal fed from a synchronous signal generator 62.

The output signal of the above mentioned CCD 49 is amplified by a preamplifier 63 forming a signal processing part 44 and is input into a double sampling circuit 65 through an isolation circuit 64 protecting the patient from electrification or the like. The double sampling circuit 65 makes double sampling to remove 1/f included in the CCD output signal and the resetting noise and makes a signal improved in S/N by removing the noise component. The signal has an unnecessary high frequency such as of a CCD carrier or the like removed through a low-pass filter (LPF) and is input into a γ-compensating circuit 67 to be γ-compensated. That is to say, the nonlinearity (usually γ=2.2) of the electrophoto converting system, when displaying with a displaying tube, is compensated and the signal is input into an A/D converter 68. The signal, converted to a digital signal by the A/D converter 68 and imaged under a frame-sequential illumination, is written into the frame memories 69R, 69G and 69B. That is to say, the signal read out of the CCD 49 is written in by one frame. That is to say, the signal transmitted, for example, through the red transmitting filter 56R, imaged under the illumination of the red light and read out is written in the frame memory 69R. When picture image data are written by one frame in the respective frame memories 69R, 69G and 69B, they will be simultaneously read out, will be respectively converted to analogue signals by the D/A converters, will further have unnecessary high frequencies removed by low-pass filters 72 and will be input respectively into horizontal outline enhancing circuits 73. The converting speed of the above mentioned A/D converter 68 and the write-in and read-out of the data in the respective frame memories 69R, 69G and 69B are controlled by the output signal by a memory controlling circuit 74. The output signal of the memory controlling circuit 74 is produced as synchronized with the synchronous signal of the above mentioned synchronous signal generator 62.

The signals compensated in the outline in the horizontal direction respectively by the above mentioned horizontal outline enhancing circuits 73 are amplified respectively by power amplifiers or output amplifiers 75 and can be output from the output ends as R, G and B three primary color signals of output impedances, for example, of 75 $\Omega$. Also, the composite synchronous signal of the synchronous signal generator 62 is output from the synchronous signal output end through the power amplifier 76.

The R, G and B outputs passed through the above mentioned respective power amplifiers 75 and the synchronous signal outputs passed through the power amplifiers 75 are input into monitors corresponding to R, G and B so that the object image may be color-displayed.

Now, in case the electronic scope 42 is fitted (connected) to the video processor 46, the signal corresponding to the number of picture elements or pixels of the electronic scope 42 to be connected must be processed. A means outputting a signal to discriminate the electronic scope is provided. In the video processor 46, the signal is taken into a scope discriminating circuit 81 and a controlling signal adapted to the discriminated scope is applied to a formed circuit in which, in case the number of picture elements varies, the frequency and characteristic must be switched in response to the number of picture elements.

Figures 11A, 11B, 11C, 12:
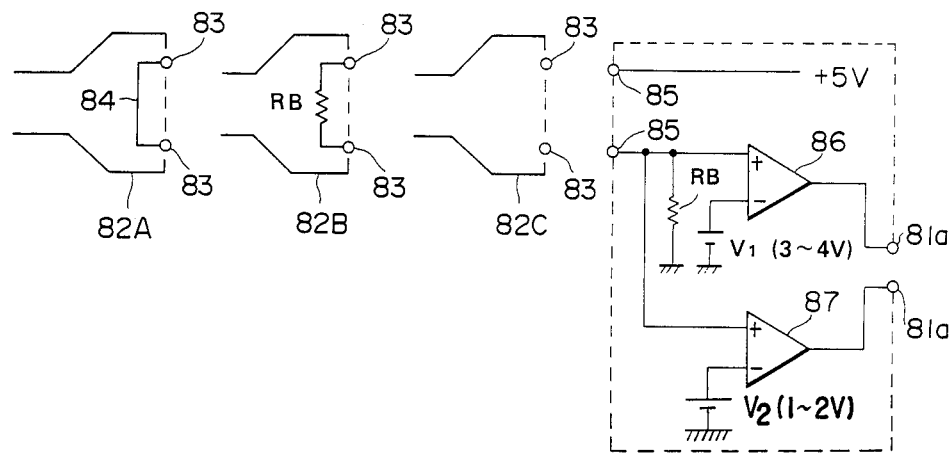

A discriminating means outputting a signal for the above mentioned discrimination and a scope discriminating circuit 81 are shown respectively in FIGS. 11 and 12.

As shown in FIG. 11, in each of connectors 82A, 82B and 82C (of respective electronic scope 42), two terminals 83 outputting a signal for detecting the number of picture elements of the scope 42 are provided (the other signal terminal is omitted). In the processor 46, the resistance value between the two terminals 83 is discriminated by the scope discriminating circuit 41 and, on the basis of the discriminated result, the part of processing the signal depending on the number of picture elements within the signal processing part 44 is switched to process the signal in response to the number of picture elements or pixels.

For example, in case there are three electronic scope respectively different in the number of picture elements, in the first electronic scope of the smallest number of picture elements, the two terminals 83 of the connector 82A are short-circuited by a lead wire 84, in the connector 82B of the second electronic scope having the second number of picture elements, the two terminals 83 are connected with each other through a resistance RB, for example, of 220 $\Omega$ and, in the connector 82C of the third electronic scope having the largest number of picture elements, the two terminals 83 are opened between them and an equivalently infinite resistance is connected.

On the other hand, as shown in FIG. 12, the scope discriminating circuit 81 has two connector receiver input ends 85, one input end 85 is connected to a current source end of +5 V, and the other input end 85 is connected to the irreversible input ends of comparators 86 and 87 and is grounded through a resistance RD, for example, of 220 $\Omega$.

A voltage V1, for example, of 3 to 4 V, is applied to the reversible input end of one comparator 86 by a standard voltage source and a voltage V2, for example, of 1 to 2 V is applied to the reversible input end of the other comparator 87 by a reference current source. The signal of two bits output from the output ends 81a of the respective comparators 86 and 87 becomes a controlling signal output in response to the number of picture elements of the scope.

In this formation, for example, if the connector 82A of the first scope is connected, the respective outputs of the comparators 86 and 87 to be controlling signals will become "H" and, if the connector 82B of the second scope is connected, the outputs of the comparators 86 and 87 will become "L" and "H". In the connector 82C of the third scope, the outputs of the comparators 86 and 87 will become "L" and "H". The control signals output through these two output lines are applied respectively to a CCD driving circuit 61, clamping pulse and sampling pulse generating circuit 88 horizontal outline compensating circuit 73, memory controlling circuit 74 and low-pass filters 66 and 77 and are processed as adapted to the number of picture elements of the connected scope. The converted clocks of the A/D converter 6 and respective D/A converters 71 are controlled by a memory controlling circuit 88.

The respective circuits controlled by the above mentioned controlling signals to process signals as adapted to the number of picture elements shall be explained in the following.

Figure 13:
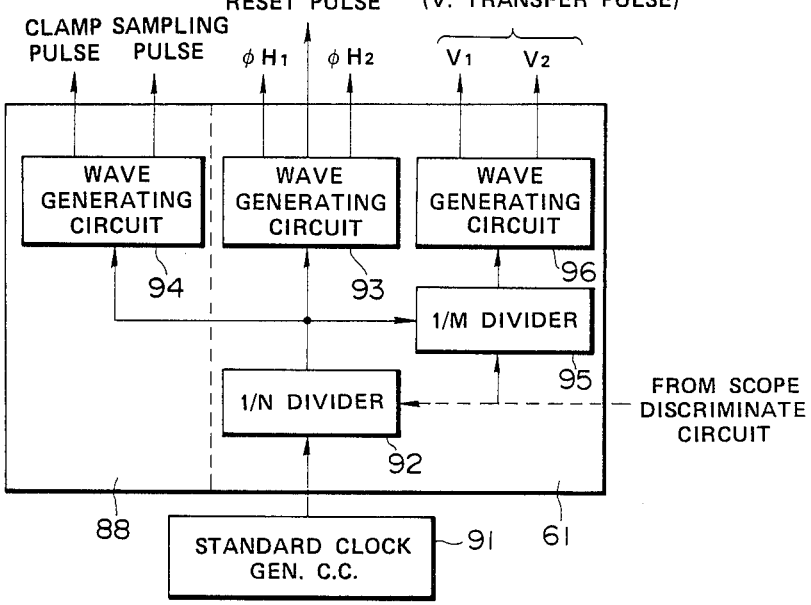

The above mentioned CCD driving circuit 61 and clamping pulse and sampling pulse generating circuit 88 are of the block formation shown in FIG. 13.

The output clock of a reference clock generating circuit 1 is divided in the frequency by a 1/N frequency divider 92 and the divided clock is input into a wave generating circuit 93 on the CCD driving circuit 61 side and also into a wave generating circuit 94 forming a double clamping pulse generating circuit 88. The divided clock is further divided in the frequency through a 1/M frequency divider 95 of the CCD driving circuit 61 and is then input also into a wave generating circuit 96.

The above mentioned 1/N frequency divider 92 and 1/M frequency divider 95 can have the frequency dividing ratios 1/N and 1/M switched by the above mentioned controlling signal. The wave generating circuit 93 on the CCD driving circuit 61 side, into which the output clock of the 1/N frequency divider 92 is input, outputs such resetting pulse as is shown in FIG. 14a and such horizontal transfer pulse $\Phi$H1 as is shown in FIG. 14b and outputs such CCD output signal as is shown in FIG. 14c from the CCD 9. On the other hand, the wave generating circuit 94 into which the clock of the above mentioned 1/N frequency divider 92 is input and which forms the clamping pulse and sampling pulse generating circuit 88 outputs an clamping pulse such and sampling pulse as are shown in FIGS. 14d and 14e.

That is to say, the output signal read out of the CCD 49 by using the resetting pulse and horizontal transfer pulse has the resetting pulse part and feeding through part mixed in the signal part. Therefore, a clamping pulse, somewhat delayed in the phase from the above mentioned resetting pulse, and a sampling pulse, synchronized with a signal part further delayed in the phase from the clamping pulse, are produced and are applied to the double sampling circuit 65 to improve S/N by removing the noise component of the resetting pulse or the like.

The clock of the above mentioned 1/N frequency divider 92 is further input into a wave generator 96 through the 1/M frequency divider 95 to produce a vertical transfer pulse corresponding to the number of vertical picture elements.

The larger the number of picture elements of the CCD 49, the higher the frequency of the above mentioned CCD driving pulse. Therefore, the signal band of the CCD picture image signal output by the pulse will become wider, therefore the maximum frequency will become higher and therefore the intercepting frequency of the low-pass filter 66 must be also made higher. On the other hand, it is desirable to prevent unnecessary higher harmonics from mixing into the signal by reducing the intercepting frequency in case the number of picture elements is small. The same can be said of the signal in the case that the picture image signal data written into the respective memories 69R, 69G and 69B are read out and are D/A converted. Therefore, in the fourth embodiment, the filter characteristics of the respective low-pass filters 72 and 66 are changed by the controlling signal.

For example, the above mentioned low-pass filter 66 is formed as shown in FIG. 15. The signal input from the input end through the double sampling circuit 65 passes through a buffer amplifier 101 and is then input into the first, second and third low-pass filters 102a, 102b and 102c connected in series respectively with resistances Ra, Rb and Rc. The output ends of the respective low-pass filters 102a, 102b and 102c are grounded through matching resistances Ra, Rb and Rc and are connected to the respective contacts 103a, 103b and 103c of an analogue switch 103. The respective contacts 103a, 103b and 103c of the analogue switch 103 are conducted with the switching contact 103d by the controlling signal and lead the signal to the next step through a buffer amplifier 104.

The above mentioned first, second and third low-pass filters 102a, 102b and 102c cut off the frequency higher than the maximum frequency component included in the signal determined by the driving pulse used for reading out by the sampling theory for different numbers of picture elements and remove unnecessary higher harmonies.

Figure 16:
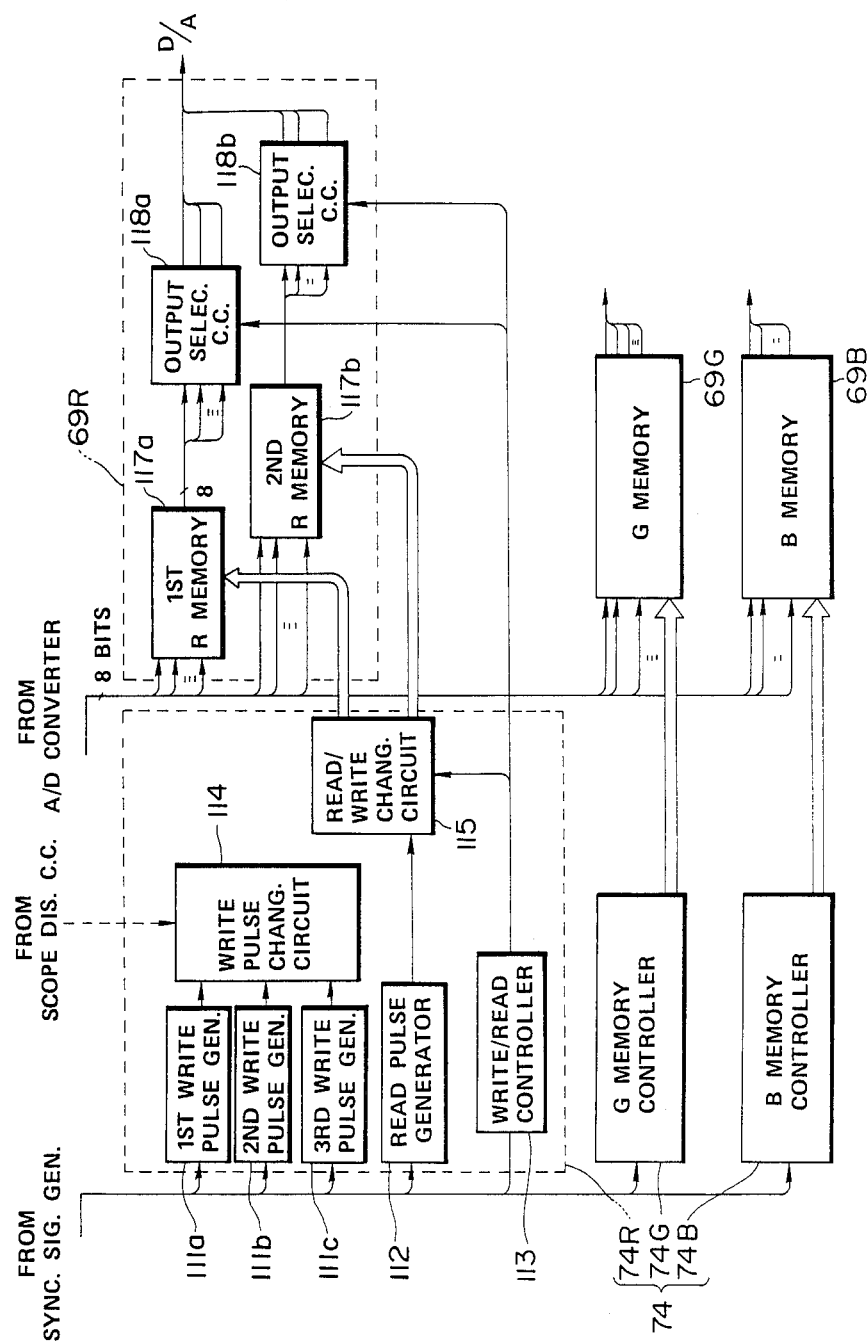

The controlling signal output from the above mentioned scope discriminating circuit 81 is input into the memory controlling circuits 74R, 74G and 74B shown in FIG. 16 and switches the timing of writing signal data into the respective R, G and B memories 69R, 69G and 69B and reading out the written signal data so as to correspond to the number of picture elements. The memory controlling circuit 74R controlling, for example, the R memory 69R shall be explained in FIG. 16. The other memories 69G and 69B and the memory controlling circuits 74G and 74B respectively controlling them are of the same formation.

The master clock of the standard clock generator within the synchronous signal generator 62 is input into the first, second and third writing pulse generators 111a, 111b and 111c forming an R memory controlling circuit 74R and also into a reading pulse generator 112 and write/read controlling part 113.

Writing pulses corresponding to the respective numbers of picture elements are generated by the above mentioned first, second and third writing pulse generators 111a, 111b and 111c and are input into a writing pulse changing circuit 114 in which the writing pulse output by the controlling signal from the scope discriminating circuit 81 is selected and is input into a read/write changing circuit 115. The read/write changing circuit 115 has two digital input ends and two digital output ends (respectively formed of a plurality of bits) and can change and output from two output ends a writing pulse input from the writing pulse changing circuit 114 side and a reading pulse input from the reading pulse generator 112 side. For example, when signal data imaged under the R illumination is input through the A/D converter 68, (for example, a writing mode signal will be applied from the write/read controlling circuit 113) the writing pulse through the writing pulse changing circuit 114 will be applied to the addressing end of the first R memory 117 so that the signal data may be written, for example, into the first R memory 117a. In this state, the reading pulse from the reading pulse generator 112 can be applied to the other second R memory 117b at a predetermined timing (the first R memory is made a writing mode in the case of the reading mode) and the signal data written in are read out. Each of the memories 117a and 117b is formed of an IC such as, for example, a dynamic RAM or static RAM.

Output selecting circuits 118a and 118b are provided respectively at the data output ends of the first R and second R memories 117a and 117b and are controlled to be on or off, for example, by "H" or "L" from the write/read controlling circuit 113. These output selecting circuits 118a and 118b are on at the time of the reading mode after being made the writing mode and the signal data read out are output on the D/A converter 71 side of the next step through the output selecting circuit 118a or 118b.

The above mentioned reading pulse generator 112 may be of the same formations as the first, second and third writing pulse generators 111a, 111b and 111c and of the writing pulse changing circuit 114 and the frequency of the reading pulse may be selected by the controlling signal of the scope discriminating circuit 81. The memory capacities of the first R and second R memories 117 and 117b are not insufficient even in the case of the maximum number of picture elements and a part of the memory capacities is used in the case of a small number of picture elements.

The same reading pulse generator 112 is used for the G memory and B memory controlling circuits 74G and 74B. That is to say, in the reading mode, the signal data written into the R, G and B memories 69R, 69B and 69B are simultaneously read out. In such a case, so that the operation in the writing mode may not be obstructed, the respective memories 69R, 69G and 69B are provided with two memories to make the writing operation and reading operation independent of each other.

The above mentioned reading mode is carried out simultaneously for the R, G and B memories 69R, 69G and 69B, three sets of the above mentioned reading pulse generators 112 need not be provided and one may be used in common.

The signal data read simultaneously out of the respective memories 69R, 69G and 69B are made analogue signals by the D/A converters 71 by which their converted clock number is controlled and are input into the respective low-pass filters 72.

The respective low-pass fillers 72 are of the same circuit formation as in FIG. 15 and the signals are controlled to be in the band corresponding to the number of picture elements and are input respectively into the horizontal outline enhancing circuits 73 which are to properly enhance the outlines in response to the number of picture elements and are formed as shown in FIG. 17. The signal input from the input end through the low-pass filter 72 is delayed, for example, by Ta by the first delaying line 121 and is then delayed also by ta by the second delaying line 122. Therefore, if the signal applied to the input end is as shown, for example, in FIG. 18a, the signals through the delaying lines 121 and 122 will be respectively as shown in FIGS. 18b and 18c. The above mentioned delaying lines 121 and 122 are fitted with taps which are connected respectively to the contacts of the analogue switches 123 and 124 so that the controlling signal of the scope discriminating circuit 81 may be applied to both analogue switches 123 and 124 to determine the selected tap. The tap selected by this controlling signal, that is, the delay amount is so set in advance as to be of a proper value in response to the number of picture elements.

The signal input from the above mentioned input end and the signal delayed by the second delaying line are added together by the first adder 125 so as to be the signal shown in FIG. 18d. The signal becomes the signal shown in FIG. 18e through a counter making $-\frac{1}{2}$ and is then input into the second adder 127. The signal through the first delaying line is also input into the adder 127. These are added together to be the signal shown in FIG. 18f. The signal is input into the third adder 129 through a variable resistance 128 for adjusting the outline enhancing amount. The signal through the first delaying line 121 is also input into the adder 129. These are added together so as to be a signal enhanced in the horizontal outline such as is shown in FIG. 18g. The signal is output to the next step side from the output end.

A resistance by which the delay amount is variable by the voltage may be used instead of the tap type delaying lines 121 and 122 used for the above mentioned delay.

In the above mentioned fourth embodiment, the case of three different numbers of picture elements has been explained. The case of two, four or more different numbers can be formed in the same manner. In the case of more than three, more than three different resistance values may be connected between the terminals 83 used to discriminate the scope. On the other hand, the number of comparators of the scope discriminating circuits may be increased. The number of terminals may be increased and many terminals may be sectioned by the combination.

Now, in the above mentioned fourth embodiment the system to be used as fitted with the electronic scope of the frame sequential imaging system has been explained.

Figure 19:
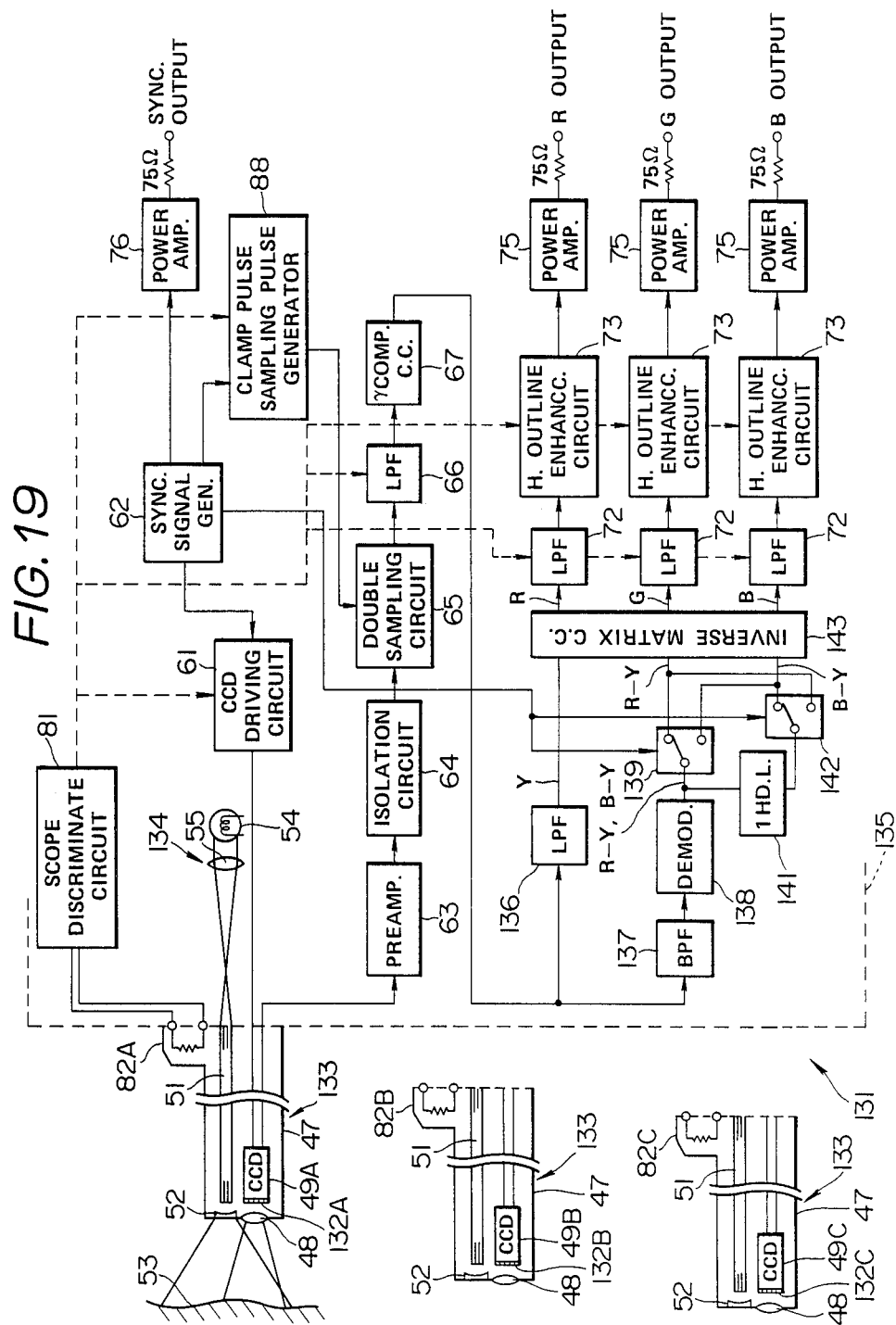
FIG. 19 is a formation diagram of a video endoscope system of the fifth embodiment of the present invention.

In the system 131 of the fifth embodiment shown in FIG. 19, there can be used a built-in color filter type electronic scope 133 in which a color separating mosaic color filter 321I is arranged in front of the imaging surface of a CCD 49I (I=A, B or C.)

In this system 131, in the fourth embodiment shown in FIG. 10, the light source part 43 is a light source part 134 having no rotary filter 16 and the white light of the lamp 54 is condensed by the lens 55 and is radiated onto the entrance end surface of the light guide 51.

In a video processor 135 in this system 131, in the signal processing part 44 shown in FIG. 10, the output of the γ-compensating circuit 67 is input into a low-pass filter 136 and a band-pass filter 137. When the output is passed through the low-pass filter 136, a luminance signal will be produced. On the other hand, when the color signal is passed through the band pass filter 137, color difference signals R-Y and B-Y will be produced in time series per horizontal line by a demodulating circuit 138. These color difference signals R-Y and B-Y in time series are input into the first analogue switch 139 and into the second analogue switch 142 through a 1H delaying line 141 delaying by one horizontal period (mentioned as 1H). When these analogue switches 139 and 141 are switched as operatively connected with each other by 1H by a switching signal synchronized with the horizontal synchronous signal, for example, of the synchronous signal generating circuit 62, respectively synchronized color difference signals R-Y and B-Y will be produced and will be input together with a luminance signal Y into an inverse matrix circuit 143 to produce R, G and B color signals. The output of the inverse matrix circuit 143 is input into respective low-pass filters 72.

The other formations are the same as in the system 41 shown in FIG. 10. The same components are represented by the same reference numerals attached to them.

In the thus formed fifth embodiment, as in the above mentioned fourth embodiment, the scope 133I to be connected can be sensed by the scope discriminating circuit 81 and the CCD driving circuit 51, double sampling circuit 65, low-pass filters 66 and 72 and horizontal outline enhancing circuit 73 are switched by the output signal of the scope discriminating circuit 81.

In the above mentioned fifth embodiment, the system 131 includes the built-in color filter type electronic scope 133I. In the system 141, as shown in FIG. 20, a built-in color filter type television camera 147 may be also fitted to an eyepiece part 146 of a fiberscope 145.

Figure 21:
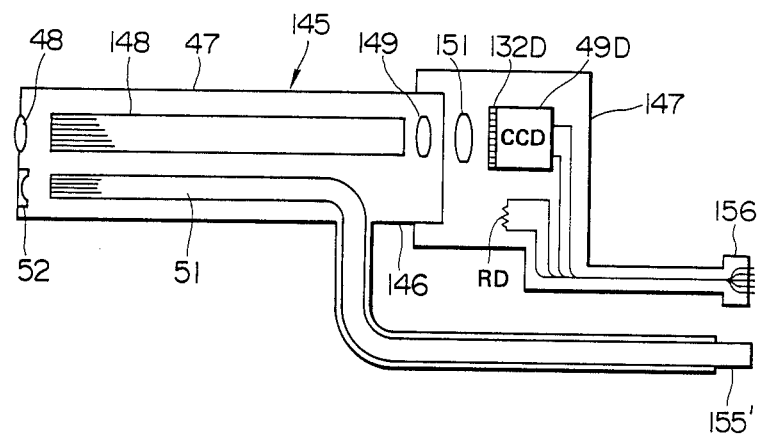
FIG. 21 is a schematic formation view of a fiberscope and television camera forming the fifth embodiment.

The above mentioned fiberscope 145 is of such formation as is shown in FIG. 21. In an electronic scope 133A shown, for example, in FIG. 19, an image guide formed of a fiber bundle 148 is used instead of the color filters 132A and CCD 49. An optical image formed on the entrance end surface of the image guide by the objective 48 is transmitted through the image guide to the exit end surface arranged on the eyepiece part 146 side and can be magnified and observed by the naked eye through the eyepiece 149 arranged opposite the exit end surface. The others are of fundamentally the same formation.

In the television camera 147 to be fitted to the eyepiece part 146, a mosaic color filter 132D is fitted to an image forming lens 151 opposed to the eyepiece 147 and an optical image is formed on the imaging surface of the CCD 49D. A resistance RD for discriminating the number of picture elements or pixels in the CCD 49D is provided within the camera 147.

Figure 20:
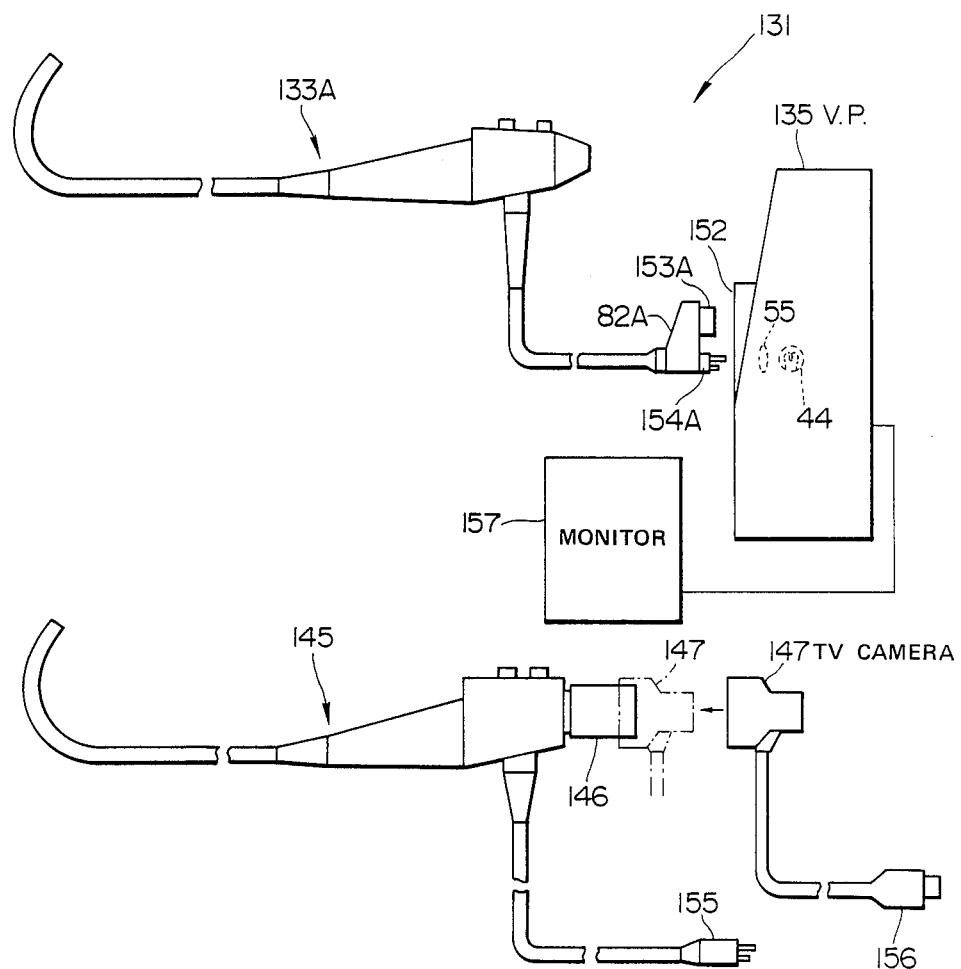
FIG. 20 is a schematic side view of the fifth embodiment.

As shown in FIG. 20, a connector receiver (receptacle) 152 is provided on the front surface of the video processor 135. The connector 82I (consisting of the signal connector 153I and light source connector 154I) of the electronic scope 133I, light source connector 155 (in fact, consisting of the light guide connector 155' and air and water feeding connector) of the fiber scope 145 and signal connector 156 of the TV camera 147 can be connected to the connector receiver 152. The signal output end of the video processor 135 is connected to a monitor 157.

Figure 22:
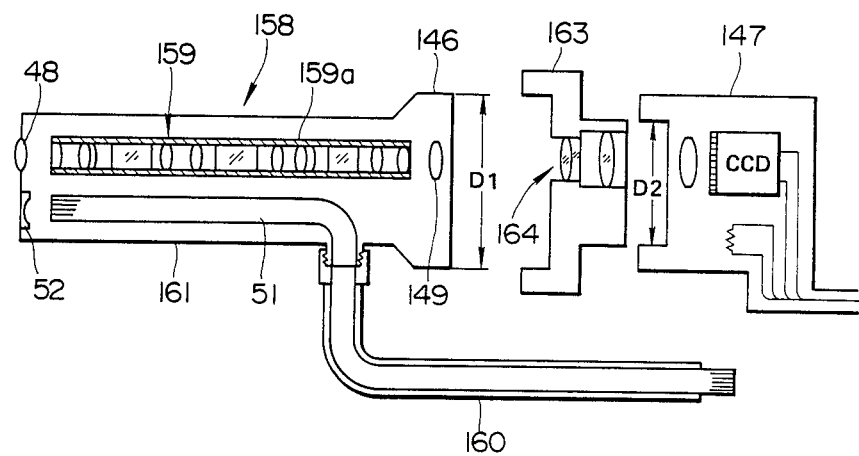
FIG. 22 is a schematic formation view of a rigid endoscope forming the fifth embodiment.

A rigid endoscope 158 shown in FIG. 22 may be used instead of the above mentioned fiberscope 145.

In the above mentioned rigid endoscope 158, an image guide shown in FIG. 21 is formed of a relay optical system 159 which is contained in such rigid optical system containing tube 159a as a metal pipe. An insertable part 160 is rigid. A light guide 51 inserted through the insertable part 160 is connected with a flexible light guide cable 161. The others are of fundamentally the same formation as of the above mentioned fiber scope 145. The same elements are represented by the same reference numerals attached to them. An optical image observed with such television camera 147 as in shown in FIGS. 20 or 21 fitted to the eyepiece part 146 of the rigid endoscope 158 is converted to an electric signal which can be color-displayed by a monitor 157. In the case of a television camera 147 of an inside diameter D2 in which, as shown in FIG. 22, the eyepiece part 146 of an outside diameter D1, the rigid endoscope 158 can not be fitted directly to the eyepiece part 146 of the fiberscope 145, an adapter 163 is interposed and the outside diameter can be varied by the adapter 163 so that the same television camera 147 may be used for both the fiberscope 145 and rigid endoscope 158. A lens system 164 for correcting the light path length in the adapter part is provided in the adapter 163. By this lens system 164, the image range formed by the CCD 49D can be made equal to that of the case of the fiberscope 145.

FIG. 23 shows a video endoscope system 171 of the sixth enbodiment of the present invention.

As shown in FIG. 23, the video endoscope system 171 of the sixth embodiment is formed of an electronic scope 172 incorporating an imaging means, a video processor 173 containing a light source means feeding an illuminating light to the electronic scope 172 and signal processing means and a monitor 174 taking in and color-displaying a video signal output from the video processor.

A flexible universal cord 177 is extended out of an operating part 176 formed as connected to the rear end of an elongated insertable part 175 of the above mentioned electronic scope 172. A connector 178 is provided in the end part of this universal cord 177. On the other hand, a connector receiver 182 making the above mentioned connector 178 connectable is provided in the video processor 173 containing the light source part 43 and a signal processing circuit 181 (See FIG. 24).

A rigid tip part 183 is provided on the tip side of the above mentioned insertable part 175 and a curvable part 184 is provided on the rear side adjacent to the tip part 183. The above mentioned curvable part 184 can be curved vertically and horizontally by rotating a curving knob 185 provided on the above mentioned operating part. An inserting port 186 communicating with a treating tool channel provided within the insertable 172 is provided in the above mentioned operating part 176.

In the signal processing part 181 of the video processor 173 in the system 171, in the embodiment shown in FIG. 10, by the output of a scope discriminating circuit 188 of a formation different from the scope discriminating circuit 81, through an R, G and B coinciding circuit 189, a white balance adjusting circuit 190 interposed between the low-pass fiber 66 and γ-compensating circuit 67 is set to be in a white balanced state corresponding to the connected scope 172. In FIG. 10, the low-pass filters 66 and 72 can be switched by the output signal of the scope discriminating circuit 81 but, in this embodiment, they can not be switched. Therefore, they are distinguished by attaching "'". Otherwise, the formation is the same as is shown in FIG. 10.

Figure 26:
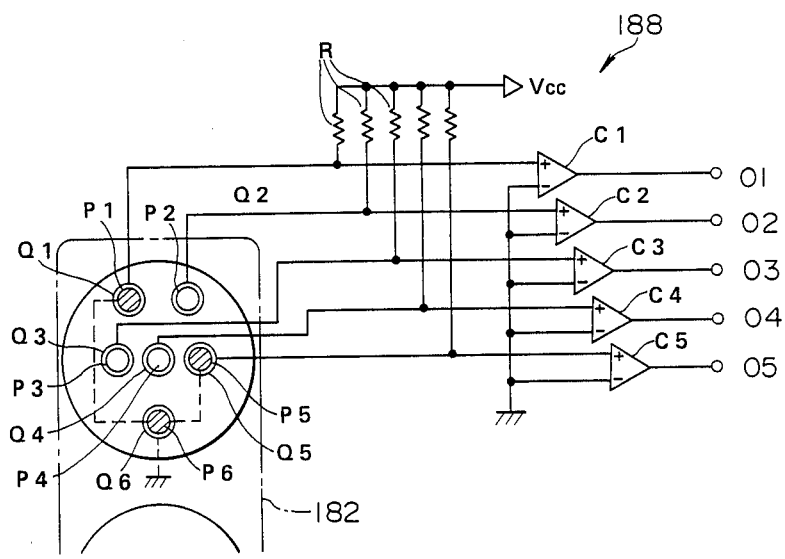
FIG. 26 is a circuit diagram of a scope discriminating circuit.

Now, in the sixth embodiment, the connector 178, fitted to the universal cord 77 of each scope 172, comprises a light source connector 191, signal connector 192 and discriminating connector 193 as shown in FIGS. 25 or 26. On the other hand, the video processor 173 has a connector receiver 182 provided with a light source connector receiver 194, signal connector receiver 195 and discriminating connector receiver 182 which can connect respectively these connectors 191, 192 and 193.

The light source connector 191 is provided in fact with an air and water feeding connector in addition to the light guide connector and these can be connected to the video processor 173. In FIG. 24, the air and water feeding means is omitted.

The above mentioned connector 178 is characterized in that the connector receiver 182 of the video processor 173 is provided with the discriminating connector 193 for discriminating the kind of the spectral characteristic of the scope 172 to be connected. By connecting the discriminating connector 193, the scope discriminating circuit 188 is used to discriminate the kind of the general spectral characteristic of the connected scope 172 and to adjust the white balance in response to the scope 172.

As shown in FIG. 26, the above mentioned discriminating connector 193 consists, for example, of six contact pins P1, P2, . . . , P6. The contact pins P1 to P5 are connected to the ground terminal P6 or are opened in response to the CCD 49 and the lengths and materials of the light guide 51 used for the scope 172.

The above mentioned pins P1 and P2 in the uppermost line are for discriminating the CCD and are used as codes for discriminating the kinds, for example, of three kinds of the CCD to be within two bits with the two pins P1 and P2.

That is to say, as the CCD is different in the spectral characteristic in response to its kind, which of the three kinds of the CCD is to be used for the scope is represented by the state of the pins P1 and P2.

Figure 27:
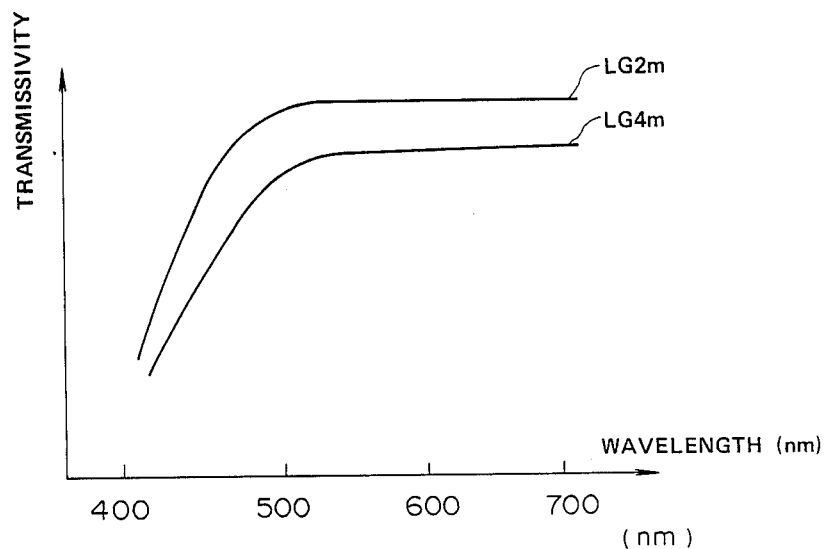
FIG. 27 is a characteristic diagram showing the transmissivity characteristic of a light guide.

The above mentioned scope length means to represent the length and material of the light guide used for the scope. As shown in FIG. 27, depending on the length (for example, 2 m and 4 m are represented respectively as LG2m and LG4m) of the light guide, the transmissivity characteristic (spectral characteristic) is different and the white balance is influenced.

Therefore, in this embodiment, the length and material of the light guide to be used for the scope are represented by the pins P3, P4 and P5 for discriminating the scope length.

With the scope 172 in this embodiment, in the discriminating connector 193 shown in FIG. 26, the pins P1 and P5 are connected to the ground terminal, the spectral characteristic relating to the scope corresponding to the connection is discriminated and the white balance is compensated to be of a compensation amount corresponding to the spectral characteristic to make the white balance.

The discriminating connector receiver 196 to which the above mentioned discriminating connector 193 is connected is provided with a scope discriminating circuit 188 as shown in FIG. 26.

That is to say, pin receivers QI to be connected with the pins PI (I=1, 2, and 5) are connected to a current source end Vcc through resistances R and also to one (irreversible) input end of each of comparators CI. The other reversible input end of each of the comparators CI is connected to the ground terminal or somewhat higher level (the ground level in the illustration). Depending on whether or not the level of one input end exceeds the reference level of the input end, a discriminating signal of "Hi" or "Low" is output. By the combination of the discriminating outputs OI of the comparators I, discriminating signals for compensating the white balance in response to the kind of the spectral characteristic of the connected scope 172 are produced. In the example in FIG. 26, as the pins P1 and P5 are connected to the ground terminal P6, the discriminating signal outputs Q1 to Q5 of the comparators C1 to C5 are "Low" in Q1 and Q5 and "Hi" in the others. Such discriminating signals are input into an RGB coinciding circuit 189 as shown in FIG. 24, produce a controlling signal varying the gain for the RGB input signals in the white balance adjusting circuit 190 and balance white.

In the above mentioned RGB coinciding circuit 189, as synchronized with the timing of inputting the R, G and B signals by the RGB changing signal input from the rotation servo circuit 59, a gain controlling signal is output in the white balance adjusting circuit 190.

Figure 28:
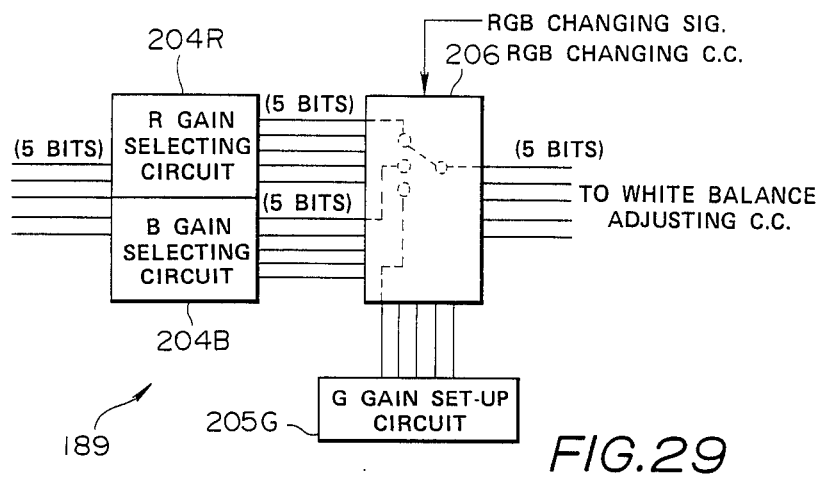
FIG. 28 is a block diagram showing a white balance adjusting part.

As shown in FIG. 28, the above mentioned RGB coinciding circuit 189 is formed of an R gain selecting circuit 204R and B gain selecting circuit 204B into which discriminating signal data of five bits output from the scope discriminating circuit 188 are input and an RGB changing circuit 106 which changes these R gain selecting circuit 204R, B gain selecting circuit 204B and G gain set-up circuit 205G and outputs gain controlling signals of five bits.

In this case, for the G signal, the gain is fixed, for example, at "1" and, for R and B signals, a gain controlling signal relatively varying them is output. In the above mentioned R gain adjusting circuit 204R, by the input discriminating signal data, an R gain controlling signal for the white balance adjustment corresponding to the spectral characteristic determined by the data is output. In other words, in order that the output data of the scope discriminating circuit 188 may correspond to the kind representing the general spectral characteristic of the scope, to what extent the gain of the R signal may be set up in the case of that spectral characteristic is written in advance into a ROM (not illustrated) and the gain controlling signal data for the R signal can be output by reading out the data written in. In this case, as the G signal is made 1, the gain controlling signal data for the R signal can be relatively determined in the magnitude by the G gain controlling signal data. The B gain selecting circuit 204B can be formed also of the same things.

Figure 29:
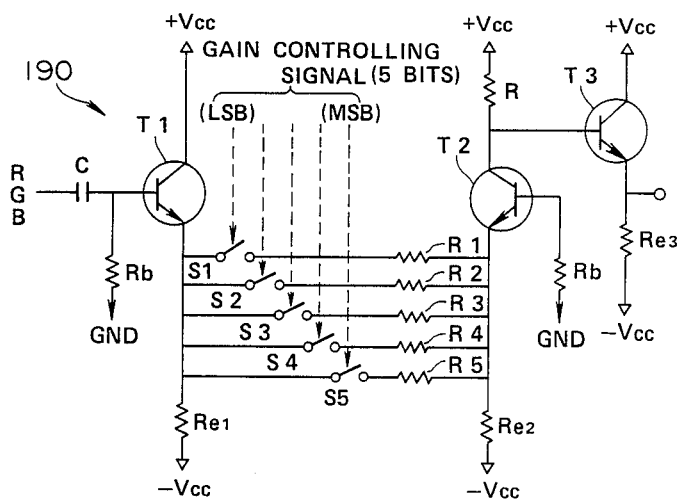
FIG. 29 is a circuit diagram showing a white balance adjusting circuit.

The white balance adjusting circuit 190 adjusting the white balance by the above mentioned gain controlling signal is formed, for example, as shown in FIG. 29.

R, G and B signals are applied through a direct current preventing condenser C to the base of one of a pair of NPN type transistors $T_1$ and $T_2$ forming a differential amplifier. The bases of the respective transistors T1 and T2 are grounded through biasing resistances Rb, the respective emitters are connected respectively to negative current source ends $-Vcc$ through resistances Re 1 and Re 2 and the respective collectors are connected to positive current source ends Vcc respectively directly and through the load resistance Rl. The collector of the other transistor $T_2$ is connected to the base of a transistor $T_3$ forming an emitter follower, the collector of the transistor $T_3$ is connected to a positive current source end Vcc and its emitter is connected to a negative current source end $-Vcc$ through a resistance Re 3 and also to the output end of the white balance adjusting circuit 190.

The emitter of the above mentioned one transistor T1 and the emitter of the other transistor $T_2$ are connected with each other through respective series circuits of a switch S1 and resistance R1, a switch S2 and resistance R2, . . . , and a switch S5 and resistance R5. These switches S1, . . . , and S5 are controlled to be on or off by gain controlling signals of five bits output from the RGB coinciding circuit 189. The combined resistance on the emitter side in case some of these resistances R1, . . . , and R5 are connected between both emitters is varied to vary the gain of the white balance adjusting circuit 190 and to adjust the white balance.

Of the above mentioned resistances R1 to R5 shown in FIG. 29, the resistance controlled to be on or off by a gain controlling signal LSB is R1 and the others are set to be $R2=R1/2$, $R3=R1/2^2$, $R4=R1/2^3$ and $R4=R1/2^4$ (R5 becomes a gain controlling signal MSB). In this case, the gain GL of the white balance adjusting circuit 190 approximates Rl/(the combined value of the resistances of R1 to R5 when on). For example, in case only the gain controlling signal LSB is "Hi" (only the switch S1 is on), $GL=Rl/R1$. In case only MSB is "Hi" (the switch S5 is on), $GL=Rl/R5$. When MSB is "Hi", the maximum gain GL will be obtained. The variation width of the gain GL is a resolution ($2^5=32$ steps) of 5 bits from Rl/R1 of LSB to Rl/R5 of MSB.

The operations of the above mentioned RGB coinciding circuit 189 and white balance adjusting circuit 190 are as follows.

Figure 30A:
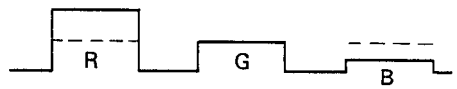
FIGS. 30a–30c are operations explaining view of a white balance adjusting circuit.

It is assumed that, for example, in case a white object is imaged, as the white is not balanced, such R, G and B signals such as are shown in FIG. 30a will be input into the white balance adjusting circuit 190.

In this case, by the connection of the connector 178 of the scope 172, a scope discriminating signal will be input into the RGB coinciding circuit 189 from the scope discriminating circuit 188, the R gain selecting circuit 204R and B gain selecting circuit 204B will output into the RGB changing circuit 206 respectively an R gain controlling signal determining the R gain when an R signal is input and a B gain controlling signal determining the B gain when a B signal is input and the G gain setting circuit 205G will also output into the RGB changing circuit 206 a G gain controlling signal for setting at 1 the gain when a G signal is input.

The RGB changing circuit 206 is made so that, at the timing when the R signal shown in FIG. 30a is input, by (the R changing signal of) the RGB changing signals, the output signal of the R gain selecting circuit 204R may be output. That is to say when the switch forming the RGB changing circuit 206 is switched, the R gain controlling signal is applied to the gain setting switches S1 to S5 of the white balance adjusting circuit 90, these switches S1 to S5 are switched on or off and the gain (R gain when the R signal is input) of the white balance adjusting circuit 90 is set at ½, the R signal in FIG. 30a will be the R signal in FIG. 30c when passed through the white balance adjusting circuit 90. Then, when the G signal is input, the switch of RGB changing circuit 206 will be switched and the gain controlling signal of the G gain setting circuit 205G will be output. Therefore, the G signal in FIG. 30a will be output at a gain of "1". The R signal is adjusted to be on the output level equal to the output level of the G signal.

In the same manner, when the B signal is input, in the white balance adjusting circuit 190 at the time when the B signal is input, for example, the B gain will be set at "2" and the B signal output from the white balance adjusting circuit 190 will become equal in the output level to the R signal and G signal.

Figure 30B:
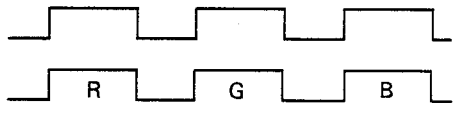
Figure 30C:
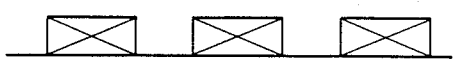

Thus, as shown in FIG. 30d, by the changing signal synchronized with the general R, G and B signals and shown in FIG. 30b, the gain will be set on a proper level and white-balanced R, G and B signals will be output.

According to the thus formed sixth embodiment, even in case the kind of the CCD in the electronic scope is different, the spectral characteristic is different and the wavelength depends on light transmitting characteristics such as the length and material of the light guide, in the connector 178 of the scope 172, a plurality of pins P1 to P6 in the discriminating connector 193 as a means for discriminating the information relating to the general spectral characteristics for the electronic scope will be opened or grounded to indicate (by encoding or the like) the spectral characteristics. Therefore, the electronic scope 172 can be made merely different in the contour in only a part of the connector from ordinary ones. Therefore, the cost of manufacturing the electronic scope is not substantially different. Also, in the case of using it, the electronic scope itself will not increase in the weight, will not become larger in the size and will be able to be prevented from becoming lower in the operatability. Also, the already sold electronic scope having no discriminating connector may be used as ever. In this case, the white balance adjusting circuit 90 may be made to be in a manual operating mode and the switches S1 to S5 may be manually adjusted to be on or off.

According to this sixth embodiment, as a color signal adjusted in the white balance in response to the general spectral characteristics of the connected electronic scope 172 is output, even if the electronic scope is not adjusted, the video image of the object can be faithfully color-reproduced.

Figure 31:
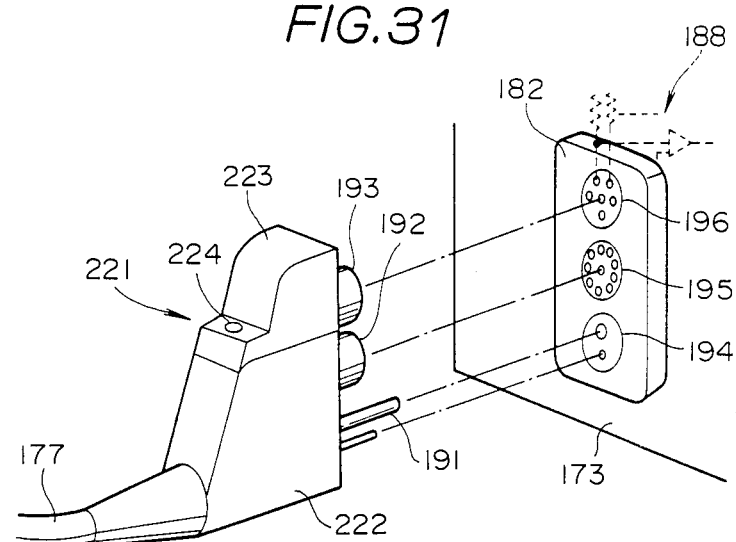
FIG. 31 is a perspective view showing a connector in the seventh embodiment.

FIG. 31 shows a connector 221 of an electronic scope in the seventh embodiment of the present invention.

As different from the existing connector 222 (having the light source connector 191 and signal connector 192) having no discriminating connector 193, in the connector 221, an adapter 223 provided with a discriminating connector can be removably fixed with a screw 224. In this case, the adapter 223 having pins P1 to P6 set to be grounded or opened in response to the electronic scope having the connector 222 may be fitted.

The others are the same as in the above mentioned sixth embodiment.

According to this embodiment, even in the case of an electronic scope having no discriminating connector 193, when the video processor 173 having the scope discriminating circuit 201 is used, the white balance will be able to be adjusted.

Figure 32:
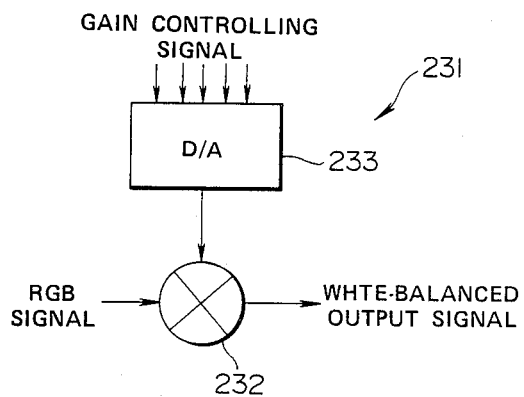
FIG. 32 is a formation view of a white balance adjusting circuit in the eighth embodiment of the present invention.
Figure 33:
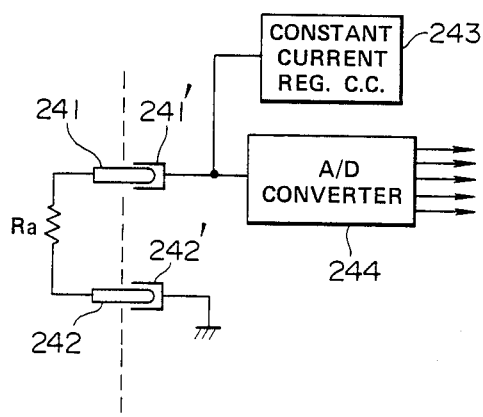
FIG. 33 is a formation view showing a scope discriminating means in the ninth embodiment of the present invention.

FIG. 32 shows a white balance adjusting circuit 231 in the eighth embodiment of the present invention.

In this embodiment, RGB signals are input into a gain controlling amplifier (abbreviated as GCA hereinafter) 232. The gain controlling signals of the RGB coinciding circuit 189 are converted to analogue signals by a D/A converter 233 and are applied to the gain controlling terminals of the GCA. By variably controlling the gain of GCA 232 with the analogue gain controlling signal applied to the gain controlling terminal, the gain of GCA 232 can be variably controlled and can be adjusted in the white balance the same as in the sixth embodiment.

FIG. 11 shows a scope discriminating means in the ninth embodiment.

In this embodiment, a resistance Ra corresponding to the scope is connected, for example, between one pin 241 of a signal connector 192 and a ground pin 242. On the other hand, a corresponding pin receiver (receptacle) 241' in the signal connector receiver 195 of the video processor 173 is connected with the output end of a constant current circuit 243 and digital data corresponding to a resistance Ra are obtained through an A/D converter 244. The pin receiver 242' of a ground pin 242 is grounded. If the output data, for example, of five bits of this A/D converter are input into the RGB coinciding circuit 189, the same operation as in the sixth embodiment will be able to be made.

Figure 34:
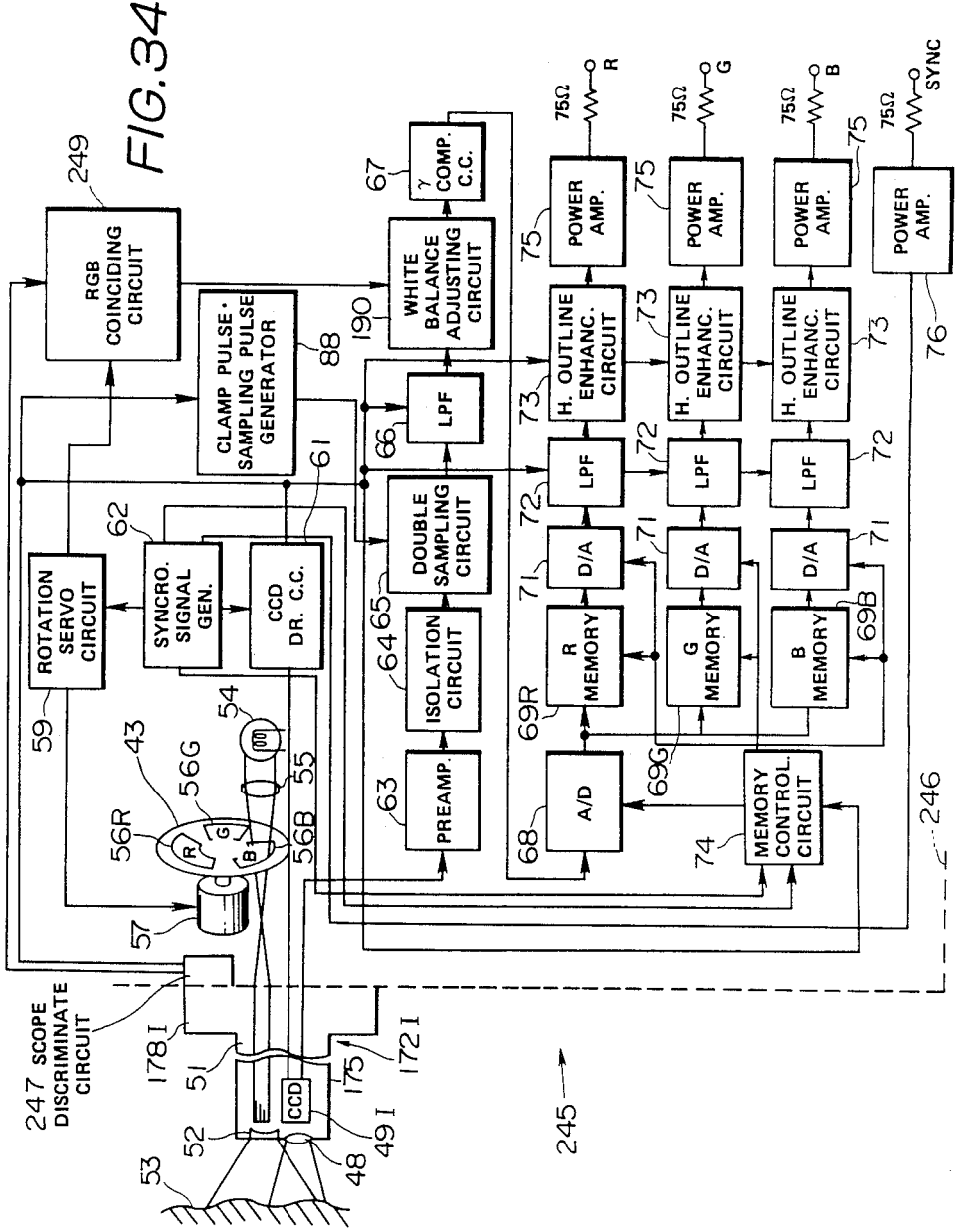
FIG. 34 is a block diagram showing the formation of a video endoscope system of the tenth embodiment of the present invention.

FIG. 34 shows the tenth embodiment of the present invention.

In a video endoscope system 245 of this embodiment, a CCDI of a different number of picture elements can be used in a electronic scope 172I.

For example, in a connector 178I of the electronic scope 172I, a discriminating connector is provided as in the above mentioned sixth embodiment. This discriminating connector is further provided with pins (not illustrated but, for example, in FIG. 26, the number of the P1 to P6 may be increased) representing the kinds of the number of picture elements of the CCD 49'. The scope discriminating circuit 247 of the video processor 246 is provided with comparators (not illustrated but, for example, in FIG. 26, the number of the comparators C1 to C5 may be increased) discriminating the kinds of the number of picture elements or pixels.

The (first) discriminating signal relating, for example, to the spectral characteristics in the discriminating signal of the scope discriminating circuit 247 is input into the PGB coinciding circuit 249 and the (second) discriminating signal for the number of picture elements of the CCD 49I in the discriminating signal is input into the driver 61, clamping pulse and sampling pulse generator 88, low-pass filter 66, three respective low-pass filters 72, memory controlling circuit 74 and three horizontal outline compensating circuits 73.

The clamping pulse and sampling pulse of the above mentioned clamping pulse and sampling pulse generator 88 are input into the double sampling circuit 65 and a signal having had a resetting noise removed is output (one of the circuits having the function of the above mentioned resetting noise removing circuit 65).

By the picture element number discriminating signal by the above mentioned scope discriminating circuit 247, a driving signal of a clock frequency and clock number corresponding to the number of picture elements of the CCD 49I is applied to the CCD 49I by the driver 61. The signal component in the signal read out of CCD 49I is sampled and extracted in the double sampling circuit 88 and only the signal band corresponding to the number of picture elements is passed through the low-pass filter 66. Also, by the memory controlling circuit 74, the A/D conversion rate of the A/D converter 68 is controlled and the clock frequency of the write-in and read-out of the memories 69R, 69G and 69B are controlled. Further, the D/A conversion rates of the respective D/A converters 71 are controlled.

The outline compensation of the respective horizontal outline enhancing circuits 73 is varied in response to the number of picture elements.

These have been already explained in FIG. 10 and their explanation shall be omitted here.

According to this tenth embodiment, even in the case of an electronic scope having a different number of picture elements, the white balance can be adjusted.

The above mentioned tenth embodiment can be applied not only to the electronic scope containing a solid state imaging device such as the CCD 49I on the tip side of the insertable part but also to the fiber scope 145 forming the image guide 148 of a fiber bundle as shown in FIG. 21 and an endoscope apparatus fitted with a television camera and containing a CCD in the eyepiece part of the rigid endoscope 158 forming an image guide of a relay optical system 159. (In this case, a frame sequential imaging system provided with no color filter in the CCD).

The signal of the information of adjusting the white balance may be output instead of the information relating to the spectral characteristics and the like provided on the electronic scope side.

Figure 35:
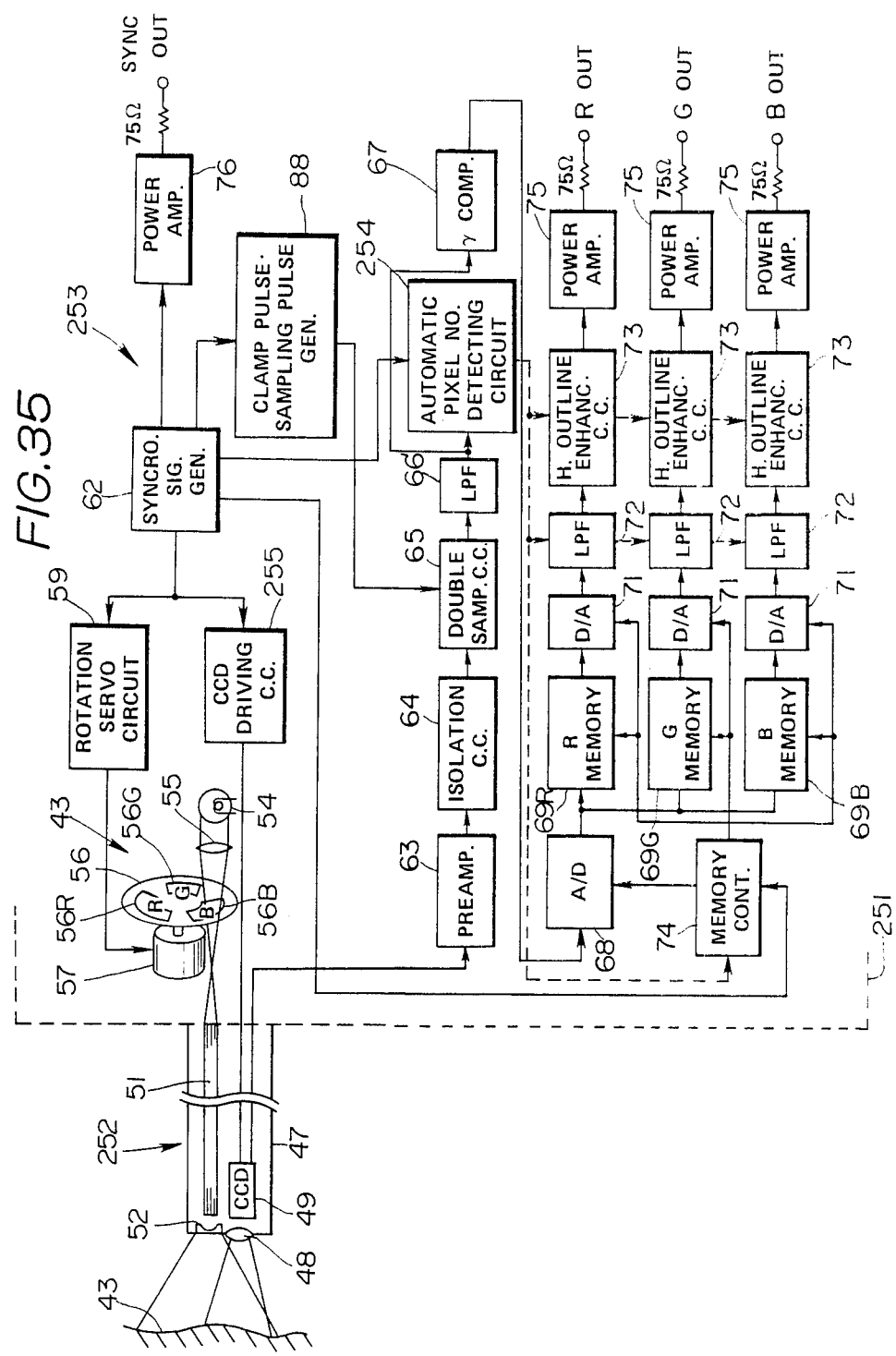
FIG. 35 is a block diagram showing the formation of a video endoscope system of the eleventh embodiment of the present invention.

FIG. 35 shows the eleventh embodiment of the present invention.

In the fourth embodiment shown in FIG. 10, a discriminating means corresponding to the number of picture elements of the scope 42 is provided in advance in each scope 42. In this embodiment, the difference in the number of picture elements can be automatically determined with the video processor 251.

Therefore, the electronic scope 252 of this embodiment has no discriminating means in the electronic scope 41 in the system shown in FIG. 10.

Also, the signal processing part 253 within the video processor 251 has no scope discriminating circuit 81 in the signal processing part 44 shown in FIG. 10 but has an automatic picture element number detecting circuit 254 wherein the characteristics of the memory controlling circuit 74, LPF 72 and horizontal outline enhancing circuit 73 are switched and controlled by the picture element number detecting signal (picture element number discriminating signal).

In this embodiment, even in case the number of picture elements is different, a driving signal of a single driving frequency will be output.

The others are the same as in the signal processing part 44 shown in the above mentioned FIG. 10. Also, the light source part 43 is exactly the same as is shown in FIG. 10.

An automatic picture element number detecting circuit 254 detecting the type of picture elements of the electronic scope 252 connected to the video processor 251, is provided in the next step of LPF 66' through which the signal is input.

By the automatic picture element number detecting circuit 254, the number of picture elements of the CCD 49 within the connected electronic scope 252 is detected. By the detected output signal, the frequency characteristics of the LPF 72 and horizontal outline enhancing circuit 73 are switched, the memory controlling circuit 74 is controlled and the characteristic optimum to the detected number of picture elements is controlled to be set.

The above mentioned automatic element number detecting circuit 254 is to drive the CCD 49 by fundamentally the same clock frequency and the width (number of picture elements) in the horizontal direction or the number of horizontal lines (width in the vertical direction (number of picture elements)) of the output signal of the CCD 49 in such case may be sensed. In this eleventh embodiment, the numbers of picture elements in the horizontal direction and vertical direction are discriminated to improve the detecting precision.

In the case of driving the above mentioned CCD 49, ""white" on the entire surface" is the best for the object to be imaged. However, in this eleventh embodiment, the maximum value is detected and therefore is not limited. In the case of an object ""white" on the entire surface", for example, in the video endoscope apparatus formed to adjust the white balance in the case of use, the white balance can be adjusted simultaneously with the operation.

Figure 36:
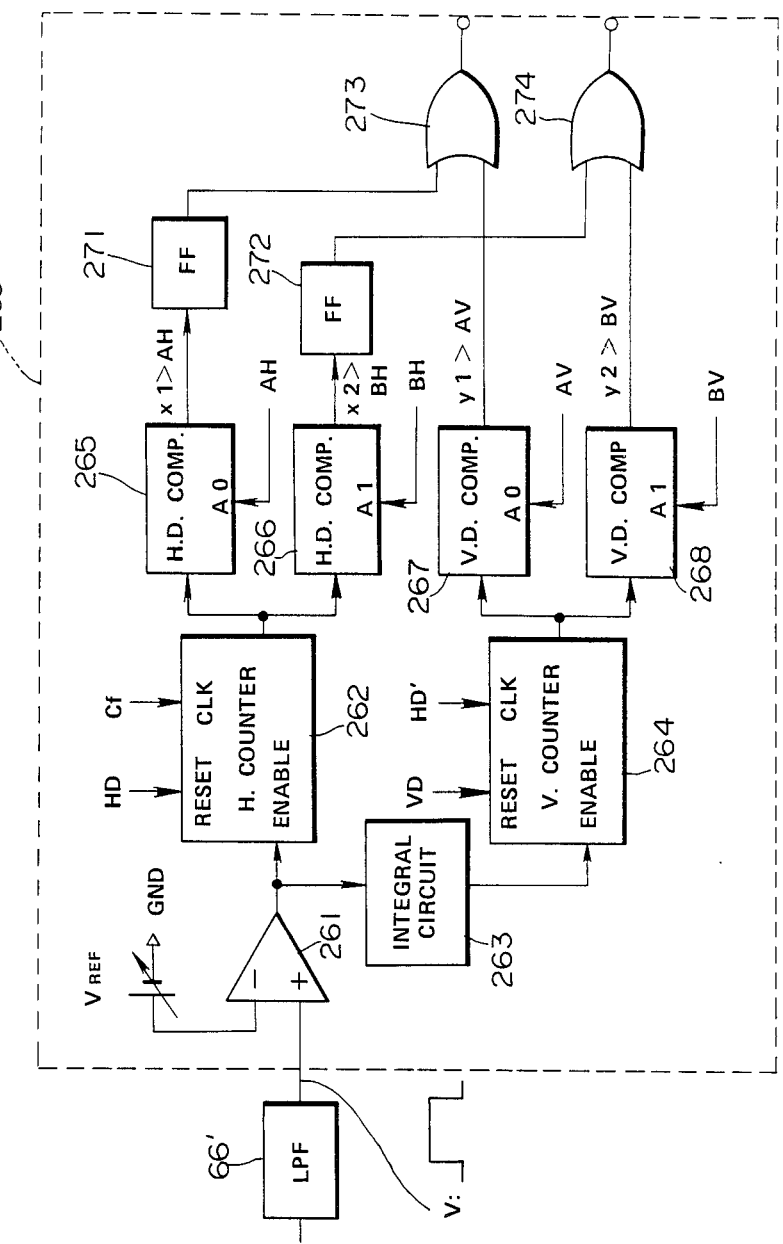
FIG. 36 is a formation diagram of a pixel number automatically detecting circuit.

The concrete formation of the above mentioned automatic picture element number detecting circuit 254 is shown in FIG. 36.

Figure 37:
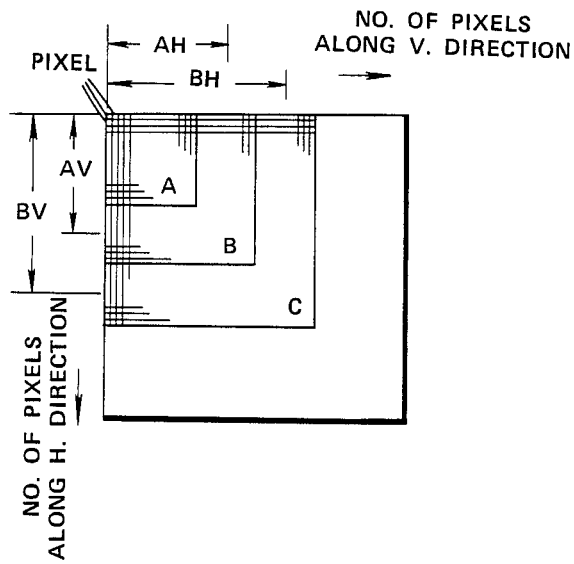
FIG. 37 is an explanatory diagram showing three kinds of picture element numbers.

Here, in this embodiment, the case of (three electronic scopes provided with) CCD's of three kinds of different numbers A, B and C (A<B<C) of picture elements as shown, for example, in FIG. 37 shall be explained.

As shown in FIG. 36, a video signal V having passed through the LPF 66' is applied to one (irreversible) input end of a comparator 261, is compared with a reference voltage level $V_{REF}$ applied to the other input end of the comparator 261 and is converted to be on a TTL level or the like easy to process in a later step. (The pulse width is the same as of the input video signal). The pulse-like signal having had the waveform shaped in the comparator is applied to a counting enabling terminal of a horizontal counter 262 and to a counting enabling terminal of a vertical counter 264 through an integral circuit 263. A clock Cf and horizontal synchronous signal HD' of a frequency f applied respectively to the clock input end for the period in which the above mentioned pulse-like signal is "1" are counted and the counted values are output from the output end.

Figure 38A:
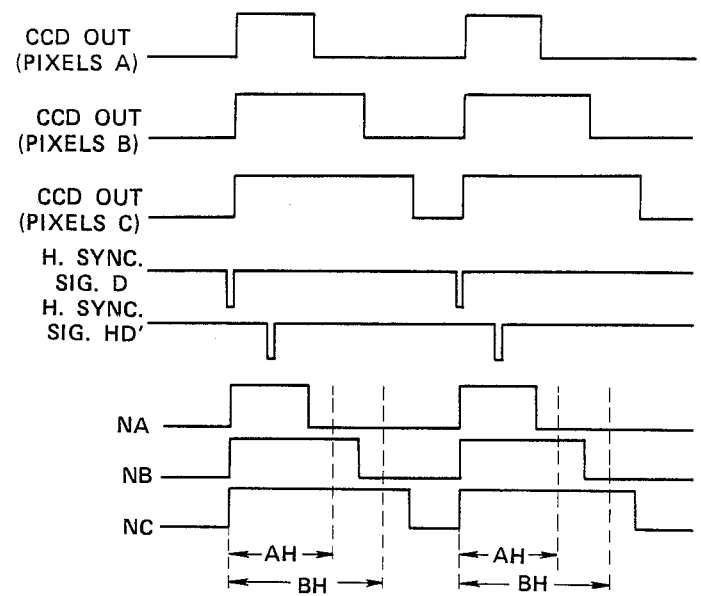
FIG. 38 is an operation explaining diagram of a pixel number automatically detecting circuit.

In the above mentioned horizontal counter 262, by the timing shown in FIG. 38A, the horizontal synchronous signal HD is applied to a resetting terminal and the clock Cf input within the period during which the HD is counted.

In this embodiment, the clock Cf is, for example, a CCD read-out signal but may be, for example, a synchronized clock (for example, a subcarrier f=3.57945 MHz) or the like under the condition of the frequency <<f of HD generated by the synchronous signal generator 62. The clock Cf is counted by the pulse width of the video signal V by the horizontal counter and is output. In the same manner, the horizontal synchronous signal HD is counted by the pulse width in the vertical direction of the video signal by the vertical counter 264 for the period after it is reset by the vertical synchronous signal VD applied to the resetting terminal and until it is next reset and the counted output, that is, the number of H lines in the vertical direction is detected. In an integral circuit 263 in the front step of the vertical counter 264, when the time constant of the integration is about 1H and a video signal exists within each horizontal period, the video signal will be (of "1" level) connected over the horizontal period and will be used as a pulse for detecting the number of H lines.

The above mentioned horizontal synchronous signal HD' is set near the center of the smallest number of picture elements in the horizontal direction. (This setting is considered to make the detection positive in order to operate the electronic scope 252 so that the observed object may be displayed generally in the central port of the picture surface but is not necessarily limited to it.)

The counted outputs of the above mentioned horizontal and vertical counters 262 and 264 are input respectively into a pair of horizontal digital comparators 265 and 266 and a pair of vertical digital comparators 267 and 268 to discriminate either of the picture element numbers A, B and C.

The digital values AH, BH and AV, BV applied respectively to the reference input ends in the above mentioned comparators 263, 264 and 265, 266 are set as in the following:

(1) AH and AV: Horizontal and vertical set values larger than (the values in the horizontal and vertical directions of) the minimum picture element number A and taking the values until the next picture element number B.

(2) BH and BV: Horizontal and vertical set values larger than the picture element number B and taking the values until the picture element number C.

The output ends of the above mentioned horizontal digital comparators 265 and 266 are connected respectively to the input ends of flip-flops (FF) 271 and 272 to hold the output values of the comparators 265 and 266 so that, once the respective outputs x1 and x2 of the comparators 265 and 266 become $x1>AH$ or $x2>BH$, the determined, that is, the value of $x1>AH$ or $x2>BH$ may be prior determined.

A means of reducing the errors in reading out when the light distributing characteristic is low or under a low illumination is provided by providing the above mentioned flip-flops 265 and 266.

In the above mentioned horizontal direction, the number of picture elements is discriminated by using the flip-flops 265 and 266. Further, in the vertical direction, the number of picture elements is discriminated by using the vertical comparators 267 and 268 (without using the flip-flops). That is to say, the output y1 of the comparator 267 discriminates whether $y1>AV$ or not and the output y2 of the comparator 268 discriminates whether $y2>BV$ or not.

The output of the above mentioned flip-flop 271 and the output of the comparator 267 prior select by an OR circuit 273 the value of the picture element number determined to be largest in the horizontal and vertical directions so that, even when the above mentioned light distribution is narrow or the illumination is low, the detection errors will be reduced by this means.

In the same manner, the output of the flip-flop 272 and the output of the comparator 268 determined prior by an OR circuit 274 the value of the picture element number determined to be largest as a result of the determination of the picture element numbers in the horizontal direction and vertical direction.

FIG. 38A shows relations between the signal input into the horizontal counter 262 and the horizontal synchronous signals HD and HD' in the case of three picture element numbers.

In the case of the minimum picture element number A, the counted value NA counted by the horizontal counter 262 will be smaller than the set value AH (needless to say, smaller than BH). That is to say, $NA<AH$, $NA<BH$ and the outputs of the comparators 265 and 266 will be "0". In the case of the picture element number B, the counted value NB counted by the horizontal counter 262 will be larger than the set value AH and will be smaller than the set value BH. That is to say, $NB>AH$ and $NB<BH$ and the outputs of the comparators 265 and 266 will be respectively "0" and "1".

In the same manner, in the case of the picture element number C, the counted value NC of the horizontal counter 262 will be larger than both set values AH and BH. That is to say, the outputs of the comparators 45 and 46 will be "1".

FIG. 38A shows also the horizontal synchronous signal HD' set substantially near the center of the minimum picture element number A (to make it easy to understand).

Figure 38B:
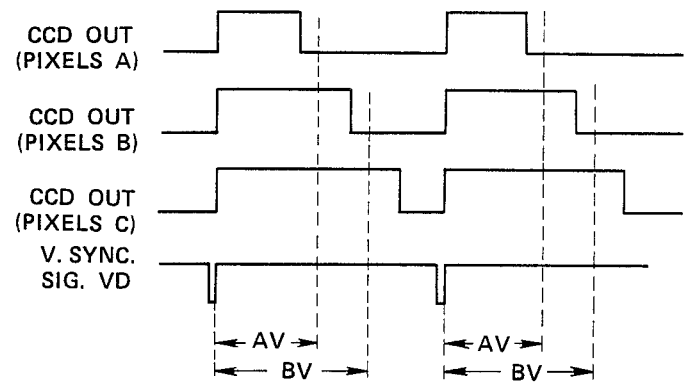

On the other hand, FIG. 38B shows that the picture element number can be discriminated also in the vertical direction in the same manner. The picture element number is discriminated the same as is explained in FIG. 38A and therefore its explanation shall be omitted. (That is to say, in case the numbers of the picture elements are A, B and C, the comparators 267 and 268 will output respectively "0" and "0"; "1" and "0"; and "1" and "1".

Figure 39:
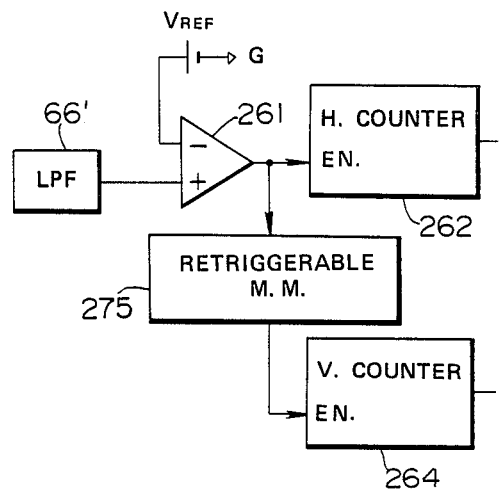
FIG. 39 is a block diagram showing a part of a pixel number automatically detecting circuit using a multivibrator instead of an integral circuit in FIG. 36.

Therefore, in the case of the picture element numbers A, B and C, the outputs of the OR circuits 273 and 274 will be respectively "0", "0"; "1", "0" and "1", "1". Therefore, in case the picture element numbers are different by the outputs of both OR circuits 273 and 274, the part required to be switched to the characteristic adapted to the picture element number will be used for a switching signal switching it. The video signal may be changed to a signal containing over a 1H period by using a retriggerable monostable multi-vibrator 275 as shown in FIG. 39 instead of the integral circuit 263 in FIG. 36. (Needless to say, the outputs will be 0 after the period when no video signal is output.)

Now, in this embodiment, even in case the number picture elements different, the clock frequency of the driving signal to the CCD 49 will be the same and the signal will be read out by the same block. The signal read out of the CCD 49 by the driving signal is double-sampled in the double-sampling circuit 65 by the pulse of the clamping pulse and sampling pulse generating circuit 88 and is output.

This manner is the same as is shown in FIG. 14. However, when the number of picture elements is different, there will be a period when no CCD output signal is output in fact.

By the output signal of the picture element number automatically detecting circuit 253, the memory controlling circuit 74 switches the frequencies of the readout clocks of the memories 69R, 69G and 69B.

The formation of the above mentioned memory controlling circuit 74 is shown in FIG. 40. In FIG. 40, for example, the memory controlling circuit 74R controlling the R memory 69R shall be explained. The other memories 69G and 69B and the memory controlling circuits 74G and 74B controlling the memories respectively are of the same formations.

The master clock of the standard clock generator within the synchronous signal generator 62 is input into the first, second and third reading pulse generators 281a, 281b and 281c forming the R memory controlling circuit 74R' and also into the writing pulse generator 282 and write/read controlling circuit 283.

The above mentioned first, second and third reading pulse generators 281a, 281b and 281c generate reading pulses corresponding to the respective numbers of picture elements and the pulses are input into the reading pulse changing circuit 284 in which the output reading pulse is selected by the changing signal from the picture element number automatically detecting circuit 253 and is input into the read/write changing circuit 285. The read/write changing circuit 285 has two digital input ends and two digital output ends (respectively formed of a plurality of bits) so that, by the output signal of the write/read controlling circuit 283, the reading pulse input from the reading pulse changing circuit 284 side and the writing pulse input from the writing pulse generator 282 side may be output as changed from the two output ends.

The LPF 27 and horizontal outline compensating circuit 73 are respectively of exactly the same formations as are shown in FIG. 17. (However, the output signal of the picture element number automatically detecting circuit 253 is used instead of the output signal of the scope changing circuit 81.)

In the above mentioned eleventh embodiment, the case of three different numbers of picture elements has been explained. The case of two, four or more different numbers of picture elements can be formed in the same manner. In the case of more different numbers of picture elements, the two digital comparators 265, 266 and 267, 268 in FIG. 36 may be made three or more. (In the case of detecting on one side only, the comparators on this side only may be made three or more.)

Now, in the above mentioned eleventh embodiment, the system to be used as fitted with the electronic scope of the frame sequential imaging system has been explained. However, even in the case of an electronic scope of a build-in filter system wherein a mosaic filter or the like is arranged in front of the imaging surface of the CCD 49 under a white illumination, the present invention can be applied in the same manner to the electronic scope in which the number of picture elements is different. In this case, in case a clock of the same frequency is to be used even in case the number of picture elements is different, the read-out driving signal will be stored once in the memory. On the other hand, in case no memory is used, it is will be desirable to change the driving frequency in response to the number of picture elements so as to be made a predetermined video signal.

In the above mentioned eleventh embodiment, the read-out frequency of the CCD is made constant (identical) even in case the number of picture elements is different. However, after the number of picture element is detected, the frequency of the driving signal may be set to correspond to the number of picture elements. In this case, the parts other than the picture element number detecting part are exactly the same as in the fourth embodiment and therefore their explanation shall be omitted.

In the above mentioned embodiment, in case it is not necessary to adjust the horizontal outline or the like, the change in response to the number of picture elements or the provision of the outline enhancing circuit may be omitted. Also, in case the deterioration of the picture quality is not large, the LPF 72 may be out off at a fixed frequency.

Even in the eleventh embodiment, it is apparent that the optical endoscope 145 or 158 shown in FIG. 21 or 22 and fitted in the eyepiece part 146 with a television camera having a built-in imaging means can be used.

Figure 41:
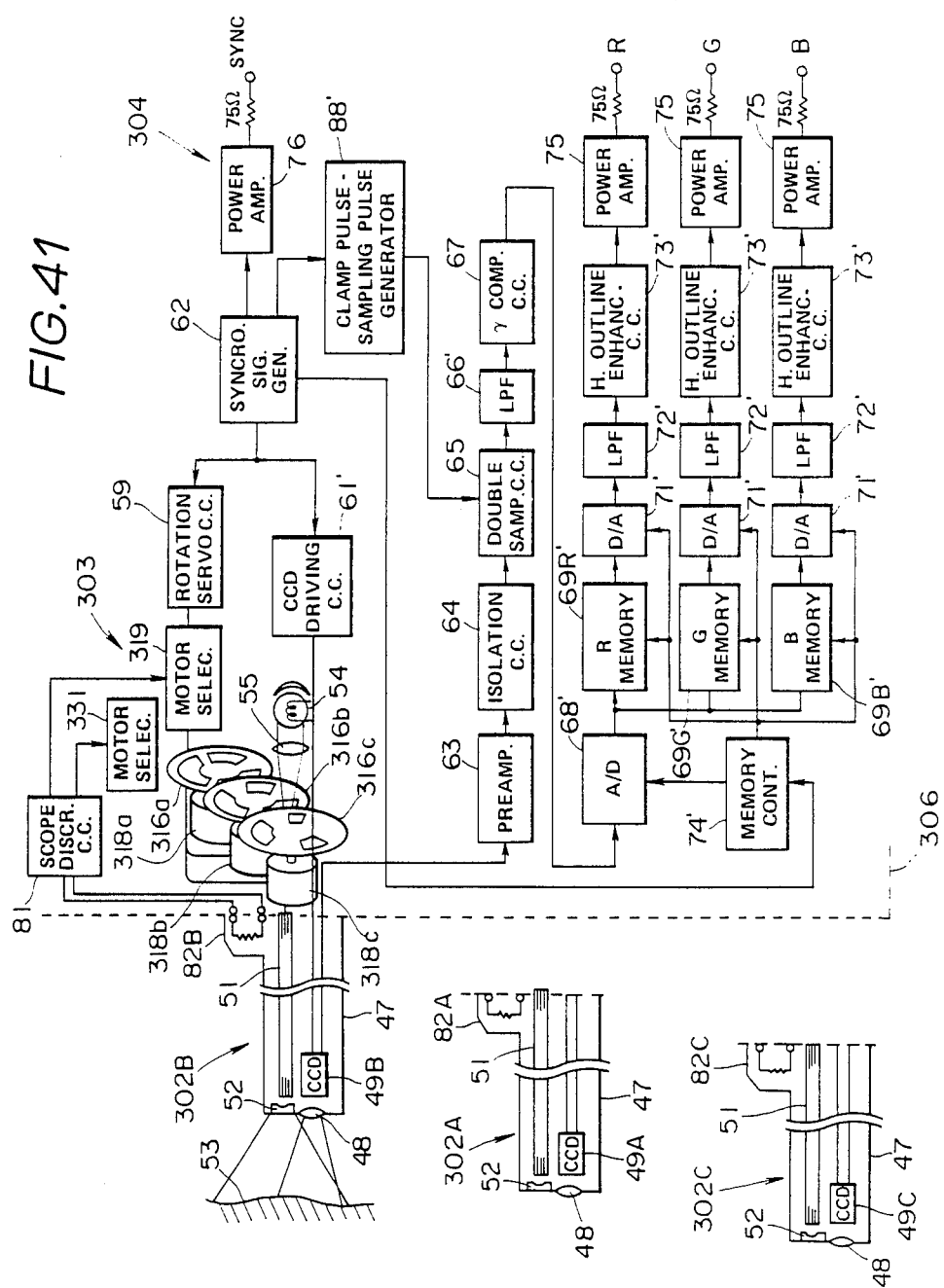
FIG. 41 is a block diagram showing the formation of the twelfth embodiment of the present invention.

FIG. 41 shows the twelfth embodiment of the present invention.

This system 301 is formed of electronic scopes 302A, 302B and 302C in which imaging means of respectively different numbers of picture elements are incorporated, a light source part 303 feeding an illuminating light to the connected electronic scope 302I (I represents I=A, B or C. In FIG. 41, 302B is connected), a signal processing part 304 converting the signal imaged by the electronic scope 302I to a video signal displayable in a displaying apparatus, a video processor 306 containing a scope discriminating means discriminating the fitted electronic scope 302I and varying the illuminating period in response to the number of picture elements of the fitted electronic scope 302I and a monitor (not illustrated).

In this twelfth embodiment, even in the case of different numbers of picture elements, signals can be processed by the same signal processing part without being switched.

Thus, if signals are processed by the common signal processing system without being switched, the circuit formation can be made very simple.

On the other hand, in case the number of picture element is different, if the signal from the CCD 49I is read out by a common driving signal, it will be necessary to set the signal reading period to the largest number of picture elements. Then, in case the number of picture elements is small, the reading period longer than is necessary will be set, the illuminating period will have to be that much shorter and therefore S/N will reduce. Therefore, in this twelfth embodiment, the reading period part becoming shorter in case the picture element number is small is applied to the illuminating period and the S/N can be improved. For this purpose, the number of picture elements is sensed and a rotary filter 316i different in the filter length is selectively used.

Figure 42:
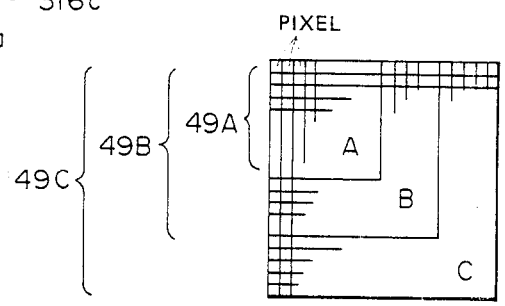
FIG. 42 is an explanatory diagram showing CCD's of three different numbers of pixels.

The numbers of picture elements of the respective electronic scopes 302I are different in the horizontal direction (lateral direction) and vertical direction (longitudinal) direction as shown in FIG. 42. The relation of the numbers of picture elements of the respective CCD 49I (represented by I) is A<B<C.

Therefore, for example, in the case of the electronic scope 302A of the smallest number of picture elements, a rotary filter 316a having the longest filter will be used. Thus, in order to select the illuminating period in response to the electronic scope 302I, the electronic scope 302I is provided with a discriminating means for discriminating the number of picture elements of the electronic scope 302I and, on the other hand, the video processor 306 is provided with a scope discriminating circuit 81.

Figure 43:
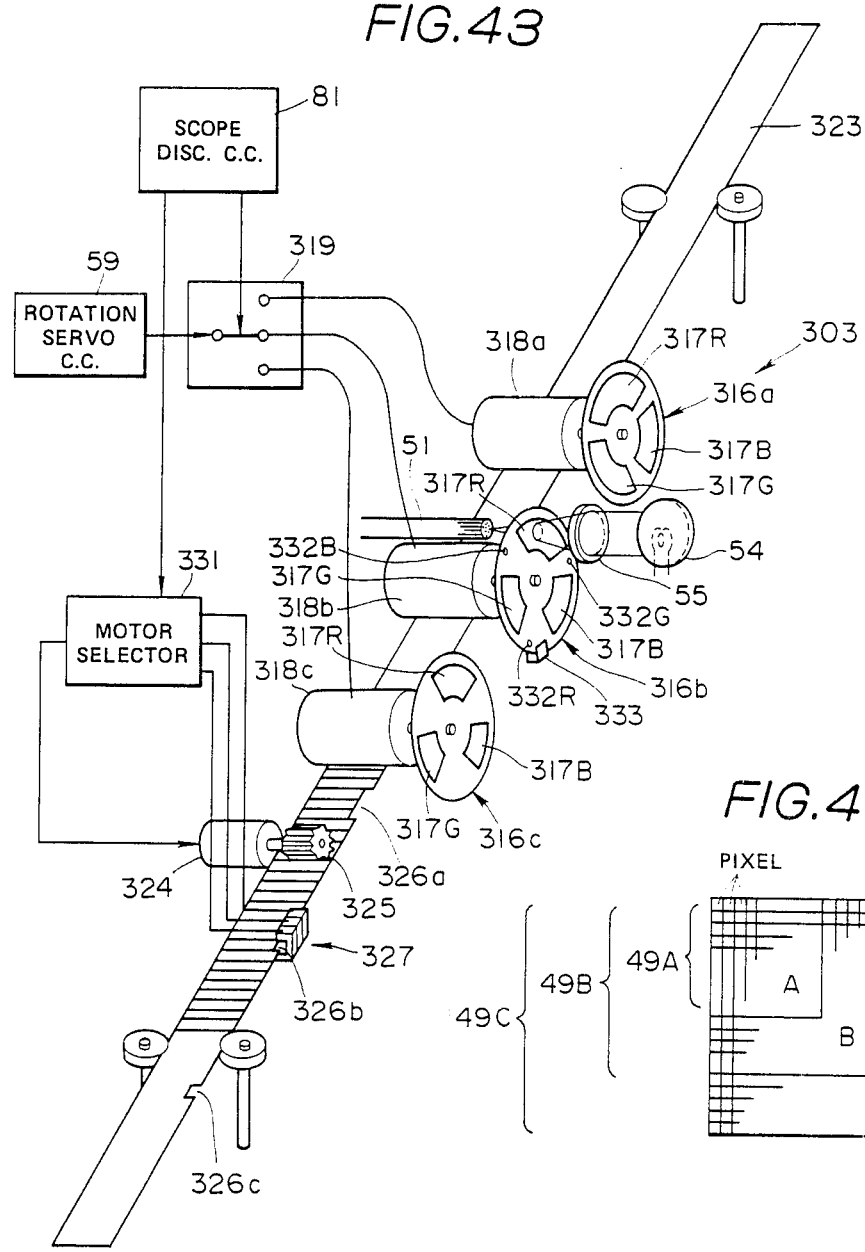
FIG. 43 is a schematic perspective view showing the formation of a light source means.

A driving signal is fed to a motor 318i rotating the rotary filter 316i interposed in the light path through a motor switch 319 by the scope discriminating circuit 81. Now, the structure of interposing in the light path one of the rotary filters 316a, 316b and 316c by the above mentioned scope discriminating circuit 81 is shown in FIG. 43.

Three motors 318a, 318b and 318c are fitted at fixed intervals, for example, on a timing belt 323 engaged with a gear 325 fitted to a rotary shaft of a moving motor 324 by the motor 324 and can be smoothly moved in the lengthwise direction of the belt 323 by guides.

Figure 44:
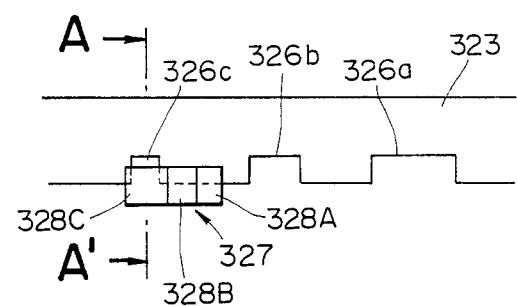
FIG. 44 is a plan view showing a position detecting means of a rotary filter.
Figure 45:
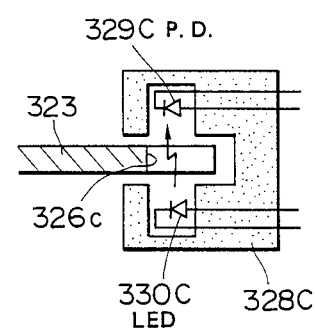
FIG. 45 is an explanatory view showing a light emitting device and light receiving device in section on line A-A' in FIG. 4.

As shown also in FIG. 44, the belt 323 is provided with incisions 316a, 326b and 326c at fixed intervals so as to be able to detect the position 9 (that is, the position of the rotary filter 316i) of the belt 323 with a position detecting sensor 327 (for example, three photointerrupters). The above mentioned incisions 326i are respectively different in the incised width and, on the other hand, the sensor 327 can discriminate the incisions 326a, 326b and 326c with the outputs of three sensor elements 328A, 328B and 328C each sensor element 328I (I=A, B or C) comprises an LED 329I and photodiode 330I as shown in FIG. 5). That is to say, the motor 324 is controlled to move for a fixed distance and either of the incisions 326a, 326b and 326c is in a position to be sensed by the sensor 327. Depending on the incised width, for example, in the cases of the shortest incision width 326c, only a diode 330C of the sensor element 328C will receive the light and the incision 326c will be able to be discriminated from the other incisions 326a and 326b. The signal of the discrimination is input into the filter switch 331 and drives the motor 324 so that the incision 326i corresponding to the discriminating signal of the scope discriminating circuit 321 may be selected. Thus, in response to the number I of picture elements of the connected scope 302I, the illuminating period is changed and, even in case the number I of picture elements is different (particularly, in case the number I is small), the signal level can be made large and an image with a good S/N can be made.

Each rotary filter 316i is provided with means for discriminating the positions of the filters 317R, 317G and 317B (for example, with small holes 332R, 332G and 332B. In FIG. 43, the small holes are shown only in the rotary filter 316b.) so that, in case a means is interposed in the light path, the timing of the illumination completion (exposure completion) of the illuminating light through the respective filters 317R, 317G and 317B may be sensed by the illuminating period completion detecting sensor 333. The output of the sensor 333 is input into the synchronous signal generator 62 to control the period (gate period) when the driving signal is applied to the CCD 49. For example, the later the output signal from the above mentioned sensor 333, the shorter the pulse number (the driving signal applying period) of the driving signal (for example, the vertical driving pulse) to the CCD 49I.

The motor 318i rotating the above mentioned rotary filter 316i is controlled in the rotation by the rotation servo circuit 359 through the motor switching circuit 319.

By the rotation servo circuit 59, the rotation of the motor 318i is synchronized in the phase with the frame frequency (29.97 Hz in the case of the NTSC system).

The object 53 illuminated frame sequentially by the above mentioned respective lights of R, G and B is imaged on the imaging surface of the CCD 49I by the objective 48. The image is transferred through the CCD by the CCD driving circuit 61' and is photoconverted to be a signal by applying to it a driving pulse for reading out of a shift register within the CCD and the signal is read out. The driving pulse and the signal of the rotation servo circuit 335 are controlled to be synchronized with the synchronous signal of the synchronous signal generator 62.

The output signal of the above mentioned CCD 49I is input into the signal processing part 304.

Now, in this twelfth embodiment, even in case the number of picture elements is different, the frequency of the driving signal to the CCD 49I uses the same (frequency) driving signal (particularly a horizontal transfer pulse). The frequency of the driving signal is set to be within the minimum frequency f MIN in case the maximum frequency operatable in the case of the CCD 49I of a different number of picture elements is different. (In the case of the CCD of the same series, the maximum frequency operatable even in the case of a different number of picture elements is the same in most cases.)

As the driving signal is thus identical, the timing of both pulses of the claming pulse and sampling pulse generating circuit 88' outputting double-sampling pulses in the double-sampling circuit is also fixed to a timing corresponding to the driving signal of the above mentioned frequency. Therefore, this double sampling circuit 65' also operates with only the minimum frequency f min and will not be switched even in case the number of picture elements is different. Even in case the number of picture elements is different, for the signal read out of any CCD 49I, the signal band of the LPF 66' will be defined by the minimum frequency f MIN of the driving signal, the spatial frequency of the obtained signal will be f MIN/2 by the theory of Nyquist and the LPE of the same characteristic of cutting off at the frequency can be used. The memories 69R', 69G' and 69B' may be set at memory capacities that can store signals from the largest number of picture elements (that is C). The memory controlling circuit 74' may be of fundamentally the same operation even in the case of a different number of picture elements. (However, in case a signal is input from the CCD 49I of a small number of picture elements, the write-in operation may be stopped for the period.)

Figure 46:
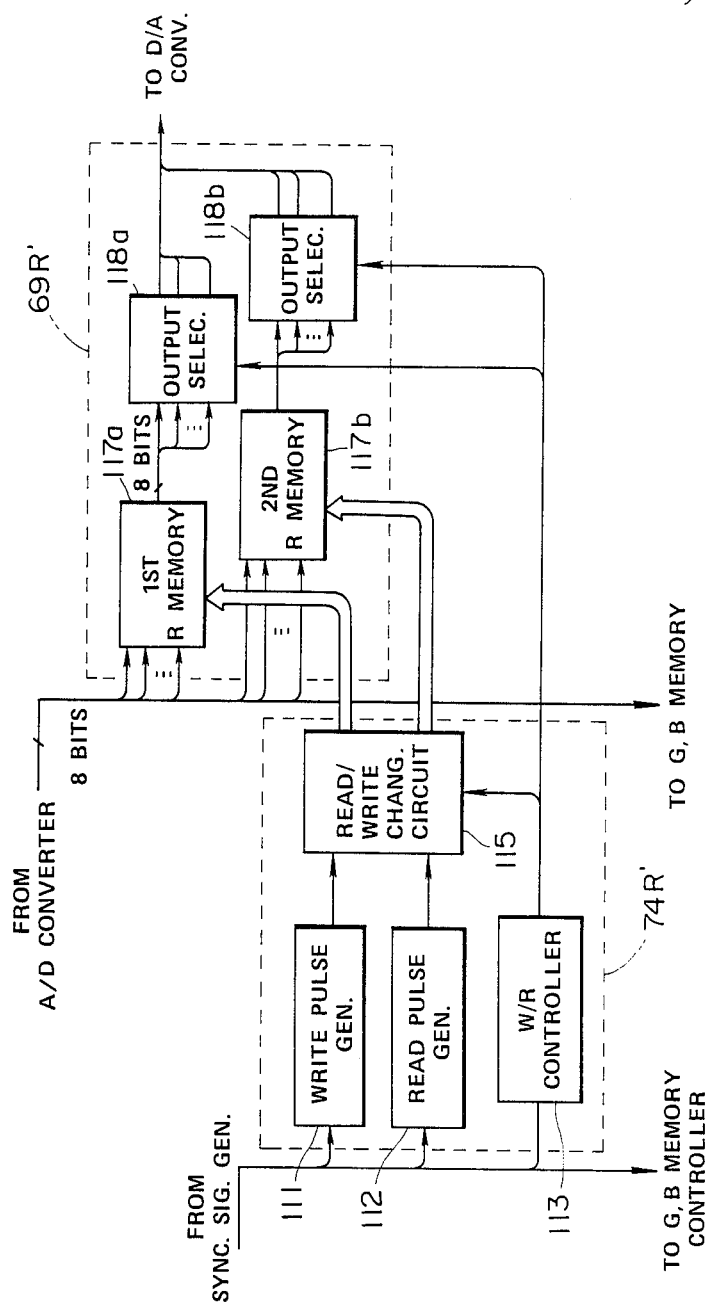
FIG. 46 is a formation diagram of a memory controlling circuit.

The formation of the memory controlling circuit 74' is shown in FIG. 46.

For example, in FIG. 16, the memory controlling circuit 74' is formed of a common writing pulse generator 111 and a common reading pulse generator 112.

It is apparent from the Nyquist theory that, in case the displayed size in the monitor may be set to be small in response to the number of picture elements for the signals read out of the above mentioned memories 69R', 69G' and 69B', the memory 69R', 69G' and 69B' readout clock, D/A converter 71' and LPF 72' need not be switched.

Further, the horizontal outline enhancing circuit 73' is fundamentally set from the characteristic of the human eye when the image on the monitor is observed at a viewing distance and need not be switched by the number of picture elements.

Even in the case of a different number of picture elements, in each CCD 49I, the signal will be read out at the same timing as is shown in FIG. 4.

According to this twelfth embodiment, in the signal processing part 304, the signal can be color-displayed on the monitor without requiring any change at all even in the case of a different number of picture elements. In case the number of picture elements is different, the illuminating period is varied and, in case the number of picture elements is small, the illuminating period is made longer than in the case that the number of picture elements is large. Therefore, S/N of the output signal can be made high.

In this twelfth embodiment, in case the number of picture elements in different, the illuminating period is varied. However, the rotary filter (316c in FIG. 43) in the case of the maximum number of picture elements may be fixed. Then, even in case the number of picture elements is different, no scope discriminating means will be required and the scope discriminating circuit 81 and filter changing means will not be required, all the circuit conditions can be made the same and a highly reliable and reasonable electronic endoscope can be formed.

In such a case, the exposure time for the CCD will be restricted by the maximum read-out period (maximum number of picture elements) and, in case a CCD of a small number of picture elements (a short read-out period) is used, S/N can not be made optimum but, as the sensitivity of the CCD is being improved, even in such a case, an electronic endoscope apparatus effective enough for the diagnosis can be provided.

Figure 47:
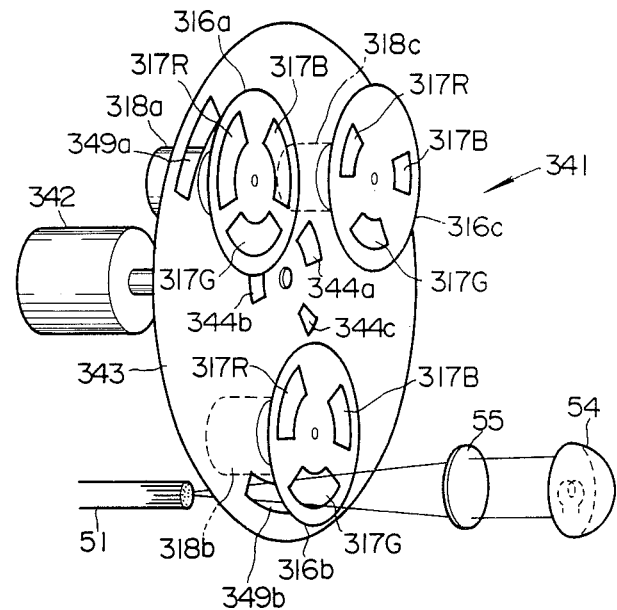
FIG. 47 is a perspective view showing a light source means in the thirteenth embodiment of the present invention.

FIG. 47 shows an essential part of the thirteenth embodiment of the present invention.

In the above mentioned twelfth embodiment, three rotary filters 316i are selectively used, whereas, in the embodiment, the light source part 341 is rotated and selected.

A rotary disc 343 is fitted to the rotary shaft of a filter changing motor 342 and three motors 318i are fitted to three places in the peripheral direction of this rotary disc 343. The same as in the twelfth embodiment, a rotary filter 316i of color transmitting filters 317R, 317G and 317B different in the length is fitted to each motor 318i.

The rotary disc 343 is provided with filter detecting reflecting plates 344i for discriminating the position of the motor 318i fitted with the above mentioned rotary filter 316i. A reflective photosensor 345 (omitted in FIG. 47. See FIGS. 48 and 49) is arranged in one place of the peripheral part opposed to these reflecting plates 344i so that, in case the rotary disc 343 is rotated, the rotary filter 316i interposed in the light path may be detected.

Figure 48:
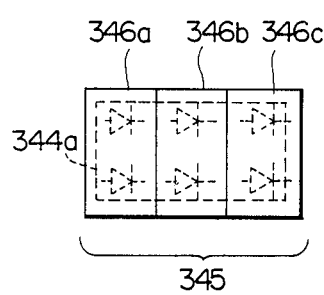
FIG. 48 is a plan view showing a position detecting means of a rotary filter.
Figure 49:
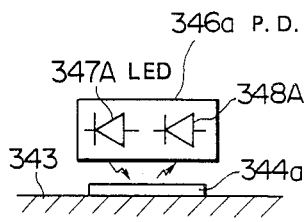
FIG. 49 is an explanatory view showing how a position is detected.

As shown in FIG. 48, the above mentioned reflective photosensor 345 consists of three photosensor elements 346i each of which consists of LED's 347I and photodiodes (or phototransistors) 348I as shown in FIG. 49 so that which rotary filter 316i is interposed in the light path may be discriminated by the number of photodiodes 348I receiving and conducting the reflected light of the LED's 347I by the reflecting plates 344i of different lengths.

The rotary disc 343 is provided with incisions 349i (which may be formed of transparent plates) in the parts facing the light path and intercepting the light when the disc is interposed in the light path so as to lead the light to the light guide 51 side.

The operations and effects of this thirteenth embodiment are substantially the same as of the above mentioned twelfth embodiment.

FIG. 50 shows a light source part 351 of the fourteenth embodiment of the present inventions. In this embodiment, an exposure time adjusting system by a servo system is adopted.

In this embodiment an exposure time adjusting filter 352 is arranged as opposed to a motor 318a fitted with a color separating rotary filter 316a having the longest filter length and is rotated by a motor 353.

The above mentioned adjusting filter 352 has apertures 354, 355 and 356 of the same length (the width is made somewhat wider) as of filters 317r, 317g and 318B in the color separating rotary filter 316a so that, when both motors 318a and 353 are rotated in the same phase, as shown in FIG. 51a, both filters 317R and 354, 317G and 355 and 317B and 356 will be rotated and driven as opposed respectively to each other and the transmitted light amount in the illumination will be maximum that is, adapted to the case of the CCD 49A of the largest number of picture elements. In the case of an intermediate number of picture elements, the motor 353 will be rotated in a phase somewhat delayed from the motor 318a and with a reference signal of the same frequency (29.97 Hz in the NTSC) and will be rotated and driven as shown in FIG. 51b. In this case, the filters 317r, 317G and 317B will have the light intercepted by the parts indicated by hatchings, the illuminating period will become shorter and the read-out period will become that much longer.

In the case of the largest number of picture elements, the phase difference of the driving signal between both motors 318a and 353 will become larger and, as shown in FIG. 51c, the unexposed part will become larger to be used for reading out.

Figure 52:
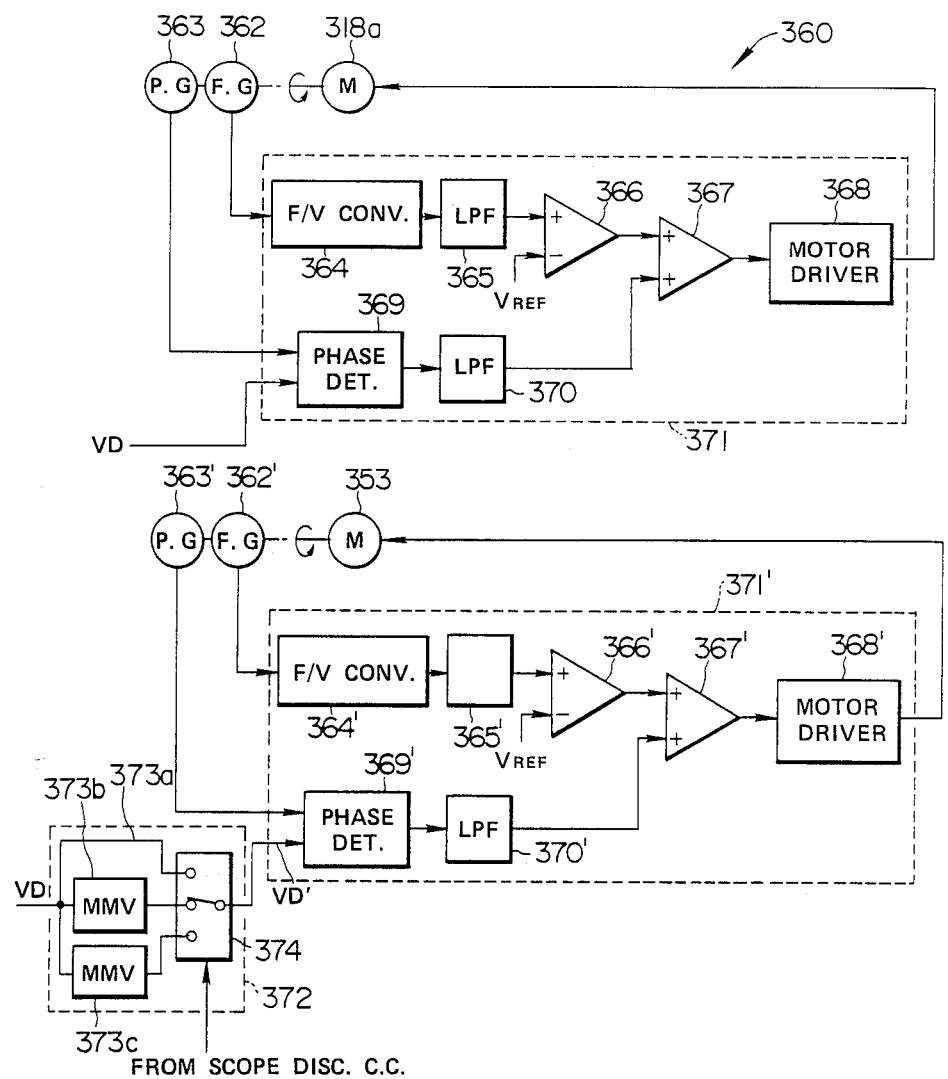
FIG. 52 is a block diagram showing the formation of an exposure time controlling means varying the exposure time by controlling the rotation phases of two motors.

The formation of a servo circuit 360 controlling the phase difference of the rotation between both motors 318a and 353 is shown in FIG. 52.

The motor 318a is mechanically connected with a frequency generator (abbreviated as F.G.) 362 and pulse generator (abbreviated as P.G.). The F.G. 362 outputs pulses of a frequency proportional to the number of rotations of the motor. Also, the P.G. 363 outputs a pulse whenever the motor 318 makes one rotation and is used to detect the rotation phase.

The output of the above mentioned F.G. 362 is input into a frequency/voltage (F/V) converter 364, is converted to a voltage proportional to the frequency, has then unnecessary components in a high range removed by an LPE 365 and is input into a differential amplifier 366. A reference voltage $V_{REF}$ is applied to the other input end of the differential amplifier 366. The differential output forms a feedback servo loop driving the motor 318a through an adder 367 and motor driver 368 and the number of rotations (about 1800 RPM in the case of the NTSC) of the motor 318a is controlled so that the difference of the above mentioned differential amplifier 366 may be "0".

On the other hand, in the system, it is necessary to synchronize the phase of the above mentioned motor 318a with the phase of the vertical synchronous signal VD. Therefore, the output of the p.G. 363 is input as a reference signal together with the vertical synchronous signal VD into a phase detector 369, has the phases of the VD and pulses (1 pulse/rotation) of the p.G. 363 compared and is added to the output signal of the differential amplifier 366 in the adder 367 through an LPF 370. By the added output, the rotation of the motor 318a is controlled to be synchronized with the VD.

The above formation is of a servo circuit 371 for the rotary filter 318a. The motor 353 fitted with the other adjusting filter 352 is controlled in the rotation by a servo circuit 371' passing the VD through a phase variable circuit 371. The components of the servo circuit are indicated by attaching "'".

The above mentioned phase variable circuit 372 consists, for example, of a line 373a outputting the VD directly together with monostable multi-vibrators (abbreviated as MMV's) 373b and 377C and a multiplexer 374 switching them so that these MMV's (or lines) 373i may be switched through the multiplexer 374 by a scope discriminating signal. The MMV's 373b and 373c are set so as to output pulses after different delay times (corresponding to the hatched parts in FIGS. 51b and 51c).

Therefore, by the servo system, for example, of the motor 318a, the vertical synchronous signal VD input into the phase detector 368 and the pulse of the P.G. 363 will be synchronized with each other as shown in FIGS. 53a and 53b. On the other hand, for example, in case an intermediate number of picture elements is selected, in the servo system on the motor 353 side, as the MMV 373b is selected, the vertical synchronous signal VD' input into the phase detector 369' will become a signal of a phase somewhat delayed as shown in FIG. 53c. Also, in the same manner, the pulse of the P.G. 363' will be of a phase D somewhat delayed from that in FIG. 53b as shown in FIG. 53d.

In the case of the largest number of picture elements, the multiplexer 374 is controlled to be switched so that the phase difference may be larger.

According to this fourteenth embodiment, the light source part 351 can be made comparatively compact.

The formation shown in FIG. 52 can be simplified by adding the driving signal driving the motor 318a to the other adjusting filter motor 353 through a delaying circuit. (In this case, the motor 353 will be open loop-controlled.) The delaying circuit may have a tap so that the tap position may be switched by a scope discriminating signal.

In the above described respective embodiments, any scope (video endoscope, fiber scope or rigid scope) has a light guide transmitting the illuminating light fed from the light source means and emitting it to the object side from the exit end surface.

Figure 54A:
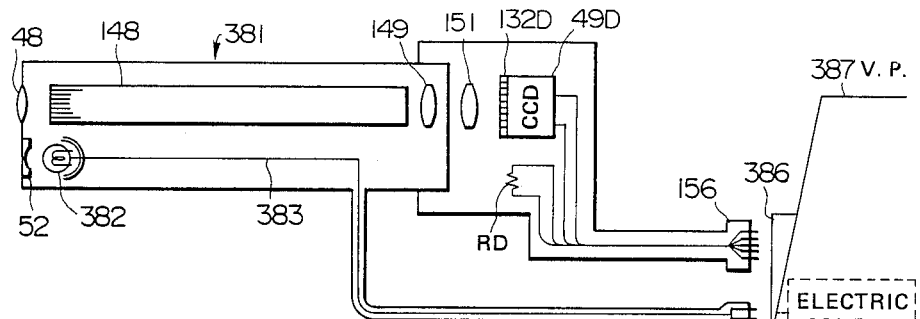
FIG. 54 is a formation view showing an essential part of a system provided with an illuminating light output means in the tip part of the insertable part.

However, the present invention is not limited to it. For example, as shown in FIG. 54a, the white lamp 382 may be contained adjacently to the objective in the tip side of the fiberscope 381 to form an illuminating light output means.

Figure 54B:
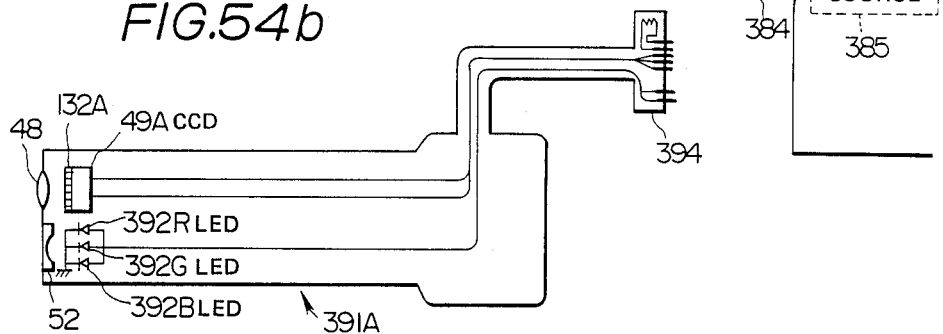

The lamp 382 is fed through the line 383 with a lighting electric power from the current source 385 by connecting the connector 384 fitted to the line 383 to the connector receiver 386 connected with the current source 385. The others are of the same formation as the fiber scope 145 shown in FIG. 21. The video processor 387 of this system is of the same formation as of the video processor 135 the system shown in FIGS. 19 and 31 wherein the light source part 134 is replaced with the current source 385. In this system, the electronic scope 391A can be also used as shown in FIG. 54b.

The electronic scope 391A is the same as the electronic scope 133A shown, for example, in FIG. 19 wherein the LED's 392R, 392G and 392B are contained instead of the light guide 51 in the tip side. These LED's 392R, 392G and 392B are LED's emitting respectively lights with the wavelengths of red, green and blue so that a substantially white illuminating light can be emitted on the object side by making them simultaneously emit lights. The LED (represented by 392) is connected to the connector 394 through the line 393 so that, when the connector 394 is connected to the video processor 387, the LED 392 will be fed with an electric power and the CCD 49A will be connected to the signal processing part. The white lamp 382 may be used instead of the LED 292.

The above described respective embodiments as partly combined also belong to the present invention.

What is claimed is:

1. A video endoscope system comprising:
   an electronic scope comprising
   an elongated insertable part,
   an illuminating light output means outputting an illuminating light out of the tip side of said insertable part,
   an imaging means formed of a solid state imaging device and having a function of imaging an object illuminated by said illuminating light output means,
   a signal transmitting cable connected with said solid state imaging device, and
   a signal connector fitted to the end part of said signal transmitting cable;
   a driving signal generating means applying a driving signal to said solid state imaging device by connecting said signal connector;
   a signal processing circuit means processing a signal read out of said solid state imaging device by the application of said driving signal;
   a displaying means displaying the video image of the object by a video signal output out of said signal processing circuit means;
   an information signal generating means provided in said electronic scope and generating an information signal relating to the number of pixels of said solid state imaging device;
   a controlling signal generating means decoding said information signal and outputting a controlling signal corresponding to said information signal; and
   a signal processing characteristic varying means forming said signal processing circuit means and varying the signal processing characteristic to correspond to the number of pixels by the application of said controlling signal.

2. A system according to claim 1 wherein said signal processing characteristic varying means varies the timing of the low-pass filter means cutting off the signal band side corresponding to said number of pixels and of the clamping pulse and sampling pulse of the double sampling circuit removing the resetting noise in the signal read out of said solid state imaging device.

3. A system according to claim 2 wherein, in case a memory means memorizing the signal output out of said solid state imaging device is within said signal processing circuit means by said controlling signal, said signal processing characteristic varying means will switch the timing frequency of at least one of write-in/read-out in said memory means in response to the number of pixels elements.

4. A system according to claim 3 wherein said controlling signal further varies the enhancing amount of the horizontal/vertical outline enhancing circuit in response to said number of pixels.

5. A video endoscope system comprising:
   an electronic scope comprising
   an elongated insertable part,
   an illuminating light output means outputting an illuminating light out of the tip side of said insertable part,
   an imaging means formed of a solid state imaging device and having a function of imaging an object illuminated by said illuminating light output means, a signal transmitting cable connected with said solid state imaging device and a signal connector fitted to the end part of said signal transmitting cable;

a driving signal generating means applying a driving signal to said solid state imaging device by connecting said signal connector;

a signal processing circuit means processing a signal read out of said solid state imaging device by the application of said driving signal;

a displaying means displaying the video image of the object by a video signal output out of said signal processing circuit means;

an information signal generating means provided in said electronic scope and generating an information signal relating to the general spectral characteristics of said electronic scope;

a controlling signal generating means sensing said information signal and generating a controlling signal for the adjustment of white balance; and a white balance adjusting means forming said signal processing circuit and capable of varying the white balance adjusting amount by the application of said controlling signal.

6. A video endoscope system comprising:
an electronic scope comprising
an elongated insertable part,
an illuminating light output means outputting an illuminating light out of the tip side of said insertable part,
an imaging means formed of a solid state imaging device and having a function of imaging an object illuminated by said illuminating light output means,
a signal transmitting cable connected with said solid state imaging device and
a signal connector fitted to the end part of said signal transmitting cable;
a driving signal generating means applying a driving signal to said solid state imaging device by connecting said signal connector;
a signal processing circuit means processing a signal read out of said solid state imaging device by the application of said driving signal;
a displaying means displaying the video image of the object by a video signal output out of said signal processing circuit;
a pixel-number automatically detecting circuit provided within said signal processing circuit means and detecting the number of pixels of said solid state imaging device from a signal read out of said solid state imaging device by the application of said driving signal; and
a processing means corresponding to a controlling signal output by said automatic pixel-number detecting circuit.

7. A video endoscope system comprising:
an electronic scope comprising
an elongated insertable part,
an illuminating light output means outputting an illuminating light out of the tip side of said insertable part,
an imaging means formed of a solid state imaging device and having a function of imaging an object illuminated by said illuminating light output means,
a signal transmitting cable connected with said solid state imaging device and
a signal connector fitted to the end part of said signal transmitting cable;

a driving signal generating means applying a driving signal to said solid state imaging device by connecting said signal connector;

a signal processing circuit means processing a signal read out of said solid state imaging device by the application of said driving signal;

a displaying means displaying the video image of the object by a video signal output out of said signal processing circuit means;

an information signal generating means provided in said electronic scope and generating an information signal relating to the number of pixels of said solid state imaging device built in said electronic scope;

a controlling signal generating means decoding said information signal and generating a controlling signal corresponding to the number of pixels; and a processing means corresponding to the number of pixels by the application of said controlling signal.

8. A system according to claim 6 or 7 wherein said processing means is formed of a signal processing character varying means provided within said signal processing circuit means and varing the signal processing characteristic to corresponding to the number of pixels.

9. An endoscope system comprising:
an optical endoscope comprising
an elongated insertable part,
a light guide means inserted through said insertable part and transmitting an illuminating light,
an observing optical system comprising an objective inserted through said insertable part and forming the image of an object illuminated by the light emitted from the emitting end surface of said light guide, an image guide having its entrance end surface arranged in the focal plane of said objective and transmitting the image of the object to the exit end surface and an eyepiece arranged as opposed to the exit end surface of said image guide and contained in the eyepiece part and
a light source connector formed on the entrance end surface of said light guide means;
an illuminating light generating means connected with said light source connector and feeding an illuminating light;
a television camera fitted to said eyepiece part of said optical endoscope and forming an imaging means of a solid state imaging device;
a signal transmitting cable connected with the solid state imaging device within said television camera;
a signal connector fitted to the end part of said signal transmitting cable;
a signal processing circuit means connectable with said signal connector, applying a driving signal to said solid state imaging device and processing the output signal of the solid state imaging device;
a displaying means displaying the video image of the object by the video signal output out of said signal processing circuit means;
an information signal generating means generating an information signal relating to the general spectral characteristic of said optical endoscope and/or television camera;
a white balance controlling signal generating means sensing said information signal and producing a controlling signal for the white balance adjustment; and
a white balance adjusting circuit means forming said signal processing circuit means and capable of varying the white balance adjusting amount by the application of said controlling signal.

10. An endoscope system comprising:
an optical endoscope comprising
an elongated insertable part,
a light guide means inserted through said insertable part and transmitting an illuminating light,
an observing optical system comprising an objective inserted through said insertable part and forming the image of an object illuminated by the light emitted from the emitting end surface of said light guide, an image guide having its entrance end surface arranged in the focal plane of said objective and transmitting the image of the object to the exit end surface and an eyepiece arranged as opposed to the exit end surface of said image guide and contained in the eyepiece part and
a light source connector formed on the entrance end surface of said light guide means;
an illuminating light generating means connected with said light source connector and feeding an illuminating light;
a television camera fitted to said eyepiece part of said optical endoscope and forming an imaging means of a solid state imaging device;
a signal transmitting cable connected with the solid state imaging device within said television camera;
a signal connector fitted to the end part of said signal transmitting cable;
a driving signal generating means connectable with said signal connector and applying a driving signal to the solid state imaging device;
a signal processing circuit means processing the signal read out of said solid state imaging device by the application of said driving signal;
a displaying means displaying the video image of the object by the video signal output out of said signal processing circuit means;
an information signal generating means built in said television camera and generating an information signal relating to the number of pixels of said solid state imaging device;
a controlling signal generating means decoding said information relating to the number of pixels and producing a different controlling signal in response to the number of pixels; and
a signal processing characteristic varying means varying the signal processing characteristic of said signal processing circuit means by the application of said controlling signal.

11. An endoscope system comprising:
an optical endoscope comprising
an elongated insertable part,
a light guide means inserted through said insertable part and transmitting an illuminating light,
an observing optical system comprising an objective inserted through said insertable part and forming the image of an object illuminated by the light emitted from the emitting end surface of said light guide, an image guide having its entrance end surface arranged in the focal plane of said objective and transmitting the image of the object to the exit end surface and an eyepiece arranged as opposed to the exit end surface of said image guide and contained in the eyepiece part and
a light source connector formed on the entrance end surface of said light guide means;

an illuminating light generating means connected with said light source connector and feeding an illuminating light;
a television camera fitted to said eyepiece part of said optical endoscope and forming an imaging means of a solid state imaging device;
a signal transmitting cable connected with the solid state imaging device within said television camera;
a signal connector fitted to the end part of said signal transmitting cable;
a driving signal generating means connectable with said signal connector and applying a driving signal to the solid state imaging device;
a signal processing circuit means processing the signal read out of said solid state imaging device by the application of said driving signal;
a displaying means displaying the video image of the object by the video signal output out of said signal processing circuit means;
a automatic pixel-number detecting circuit provided within said signal processing circuit means and detecting the number of pixels of said solid state imaging device from the signal read out of said solid state imaging device by the application of said driving signal.

12. A system according to any of claims 9, 10 or 11 wherein said television camera is of a built-in color filter type.

13. A system according to any of claims 9, 10 or 11 wherein said television camera is of a frame sequential imaging system having no built-in color filter.

14. A system according to claim 6 or 11 wherein said automatic pixel number detecting circuit has a comparator means which comparates an input signal read out from said solid state imaging device by application of said driving signal with a definite level, and a counter means which counts a clock in a period said comparator means descriminates said input signal larger than said definite level.

15. A system according to claim 14 wherein said automatic pixel number detecting circuit has second comparator means which comparates an output number of said counter means with a definite number corresponding to some number of pixels.

16. A system according to claim 15 wherein said second comparator means is formed of a digital comparator.

17. A system according to claim 6 or 11 wherein said automatic pixel number detecting circuit detects two numbers of pixels along a horizontal direction and a vertical direction.

18. A system according to any of claims 6, 7, 9 or 10 wherein said information signal generating means is formed integrally with said signal connector.

19. A system according to claim 18 wherein said information signal generating means is formed of an adapter which can be fitted to said signal connector.

20. A system according to claim 18 wherein said information signal generating means is provided within said signal connector.

21. A system according to any of claims 9 or 10 wherein said information signal generating means generates an information signal of 1 bit with each contact pin.

22. A system according to claim 21 wherein said controlling signal generating means is formed of a comparator discriminating whether the bit signal of said contact pin is on the defined level or not.

23. A video endoscope system according to any of claims 9 or 10 wherein said information signal generating means is formed of a resistance connected between contact pins.

24. A system according to claim 23 wherein said controlling signal generating means comprises a constant current circuit flowing a constant current to a connected resistance and an A/D converter converting the voltage at both ends of the resistance through which said constant current is flowed to a digital amount.

25. A system according to any of claims 9 or 10 wherein said information signal generating means is formed of read-only memories.

26. A system according to any of claim 1, 5, 6 or 7 wherein said electronic scope is of a built-in color filter type.

27. A system according to any of claims 1, 5, 6 or 7 wherein said electronic scope is of a frame sequential imaging system having no built-in color filter.

28. A system according to any of claims 1, 5, 6, 7, 9, 10 or 11 wherein said signal processing circuit means is to make a frame sequential signal processing of producing a video signal which can be color-displayed by said displaying means for the signal output out of said imaging means under a frame sequential illumination.

29. A system according to claim 28 wherein said signal processing circuit means has a first low-pass filter means cutting off unnecessary higher harmonics, and A/D converting means A/D converting the signal passed through said low-pass filter means, a digital memory means once memorizing the digital signal passed through this A/D converter, a D/A converting means D/A converting the digital signal read out of said digital memory means and a second low-pass filter means cutting off the higher harmonics of the analogue signal by said D/A converting means.

30. A system according to claim 29 herein said signal processing circuit means further has a resetting noise removing double sampling circuit arranged on the front step side of said first low-pass filter means and a horizontal/vertical outline enhancing circuit provided on the rear step side of said second low-pass filter means.

31. A system according to any of claims 1, 5, 6, 7, 9, 10 or 11 wherein said signal processing circuit means is to make a signal processing of producing a video signal which can be color-displayed by said displaying means for the signal output out of said imaging means under a white color illumination.

32. A system according to claim 31 wherein said signal processing circuit means has a first low-pass filter means cutting off input unnecessary higher harmonics, a color separating circuit arranged on the rear step side of said low-pass filter and outputting a color-separated color signal and a second low-pass filter means arranged on the read end side of said color-separating circuit.

33. A system according to claim 32 wherein said signal processing circuit means further has a resetting noise removing double sampling circuit provided on the front step side of said first low-pass filter means and a horizontal/vertical outline enhancing circuit provided on the rear step side of said second low-pass filter means.

34. A system according to any of claims 1, 6, 9, 10 or 11 wherein, even in case the number of pixels is different, said driving signal generating means will set the same the frequency of the horizontal transfer clock of said driving signal.

35. A system according to any of claims 6 or 11 wherein said exposure time controlling means changes a plurality of rotary wheels fitted respectively with a plurality of color transmitting filters to vary the illuminating time through the respective color transmitting filters.

36. A system according to any of claims 1, 5, 6 or 7 wherein said illuminating light output means is formed of a light emitting diode arranged in the tip part of the insertable part of said electroscope.

37. A system according to claim 36 wherein said signal processing means will hold the same circuit constant even in case said number of pixels is different.

38. A system according to any of claims 1, 5, 6 or 7 wherein said illuminating light output means is formed of a lamp arranged in the top part of the insertable part of said electronscope.

39. A system according to any of claims 1, 6, 7, 9, 10 or 11 wherein said controlling signal varies the frequency of the horizontal transfer clock of the driving signal by said driving signal generating means in response to said number of pixels.

40. A video endoscope system comprising:
   a plurality of electronic scopes forming imaging means of solid state imaging devices different in the number of picture elements;
   a signal cable connected to said solid state imaging device of said electronic scope;
   a connector fitted to the end part of said signal cable;
   a signal processing circuit means connected to a connector receiver connectable with said connector and processing the signal to output a video signal;
   a monitor means displaying the video signal output from said signal processing means; and
   a driving circuit applying the same driving signal even in case the number of pixels of said solid state imaging device is different.

* * * * *